US012616704B2

(12) United States Patent
Abrishami

(10) Patent No.: US 12,616,704 B2
(45) Date of Patent: May 5, 2026

(54) CANNABICHROMENE FORMULATION FOR PAIN MANAGEMENT

(71) Applicant: Zyus Life Sciences Inc., Saskatoon (CA)

(72) Inventor: Mahsa Abrishami, Saskatoon (CA)

(73) Assignee: Zyus Life Sciences Inc., Saskatoon (CA)

( * ) Notice: Subject to any disclaimer, the term of this patent is extended or adjusted under 35 U.S.C. 154(b) by 680 days.

(21) Appl. No.: 17/920,643

(22) PCT Filed: Mar. 31, 2021

(86) PCT No.: PCT/CA2021/050430
§ 371 (c)(1),
(2) Date: Oct. 21, 2022

(87) PCT Pub. No.: WO2021/212209
PCT Pub. Date: Oct. 28, 2021

(65) Prior Publication Data
US 2023/0149343 A1 May 18, 2023

Related U.S. Application Data

(63) Continuation-in-part of application No. 17/038,048, filed on Sep. 30, 2020, now abandoned.

(60) Provisional application No. 63/015,039, filed on Apr. 24, 2020, provisional application No. 63/145,040, filed on Feb. 3, 2021.

(51) Int. Cl.
*A61K 31/352* (2006.01)
*A61K 31/00* (2006.01)
*A61K 31/05* (2006.01)
*A61P 25/04* (2006.01)

(52) U.S. Cl.
CPC ............ *A61K 31/658* (2023.05); *A61K 31/05* (2013.01); *A61P 25/04* (2018.01)

(58) Field of Classification Search
CPC .............................. A61K 31/352; A61P 29/00
USPC ......................................................... 514/456
See application file for complete search history.

(56) References Cited

U.S. PATENT DOCUMENTS

| | | | |
|---|---|---|---|
| 2016/0106705 A1 | 4/2016 | Verzura et al. | |
| 2016/0360721 A1 | 12/2016 | De Meijer | |
| 2018/0193304 A1 | 7/2018 | Cranford et al. | |

FOREIGN PATENT DOCUMENTS

| | | |
|---|---|---|
| WO | 2007083098 A1 | 7/2007 |
| WO | 2008129258 A1 | 10/2008 |
| WO | 2012144892 A1 | 10/2012 |
| WO | 2012160358 A1 | 11/2012 |
| WO | 2013165251 A1 | 11/2013 |
| WO | 2016044370 A1 | 3/2016 |
| WO | 2016090287 A2 | 6/2016 |
| WO | 2020000103 A1 | 1/2020 |

OTHER PUBLICATIONS

Abid et al., "Exploring Patterns Enriched in a Dataset With Contrastive Principal Component Analysis," Nature Communications, May 2018, vol. 9, pp. 1-7.
Bates, et al., "Fitting Linear Mixed-Effects Models Using Ime4," Journal of Statistical Software, Oct. 2015, vol. 67 (1), pp. 1-48.
Colloca et al., "Neuropathic Pain," Nature Reviews, Disease Primers, Feb. 2017, vol. 3, pp. 17002.
Crippa et al., "Δ9-THC Intoxication by Cannabidiol-Enriched Cannabis Extract in Two Children with Refractory Epilepsy: Full Remission after Switching to Purified Cannabidiol," Frontiers in Pharmacology, Sep. 2016, vol. 7, pp. 359.
Crippa et al., "Translational Investigation of the Therapeutic Potential of Cannabidiol (CBD): Toward a New Age," Frontiers in Pharmacology, 2018, vol. 9, pp. 2009.
Cudalbu et al., "The C57BL/6J Mouse Exhibits Sporadic Congenital Portosystemic Shunts," Plos One, Jul. 2013, vol. 8(7), e69782.
Delong et al., "Pharmacological Evaluation of the Natural Constituent of *Cannabis sativa*, Cannabichromene and its Modulation by Delta(9)-Tetrahydrocannabinol", Drug and Alcohol Dependence, Nov. 2010, vol. 112(1-2), pp. 126-133.
Deyo and Musty "A Cannabichromene (CBC) Extract Alters Behavioural Despair on the Mouse Tail Suspension Test of Depression," Symposium on the Cannabinoids, Burlington, Vermont, International Cannabinoid Research Society, 2003, p. 146.
Elsohly and Gul., "Constituents of *Cannabis sativa*," Handbook of Cannabis, 2014, pp. 28. DOI : 10.1093/acprof:oso/9780199662685.001.0001.
Guimarhes et al., "Antianxiety Effect of Cannabidiol in the Elevated Plus-maze," Psychopharmacology, 1990, vol. 100(4), pp. 558-559.
Hou et al., "Treatment of Chemotherapy-Induced Peripheral Neuropathy Systematic Review and Recommendations," Pain Physician, Nov. 2018, vol. 21(6), pp. 571-592.
International Patent Application No. PCT/CA2021/050430, International Preliminary Report on Patentability dated Aug. 16, 2022.
International Patent Application No. PCT/CA2021/050430, International Search Report and Written Opinion dated Jun. 21, 2021.
Izzo et al., "Inhibitory Effect of Cannabichromene, a Major Non-Psychotropic Cannabinoid Extracted From *Cannabis sativa*, on Inflammation-Induced Hypermotility in Mice," British Journal of Pharmacology, 2012, vol. 166, pp. 1444-1460.
Izzo et al., "Non-Psychotropic Plant Cannabinoids: New Therapeutic Opportunities From an Ancient Herb," Trends in Pharmacological Sciences, Sep. 2009, vol. 30(10), pp. 515-557.

(Continued)

*Primary Examiner* — Charanjit Aulakh
(74) *Attorney, Agent, or Firm* — Borden Ladner Gervais LLP

(57) ABSTRACT

A formulation for pain management is provided comprising cannabichromene as the primary cannabinoid together with an excipient and, optionally, one or more secondary cannabinoids in an amount of up to 5% by weight of the primary cannabinoid. The formulation is essentially free of tetrahydrocannabinol. The types of pain to be managed with the formulation include but are not limited to the treatment of neuropathic pain, pain due to cancer, injury, accident, surgery, or tissue damage. Methods of use of the formulation, doses and dosage forms are described.

14 Claims, 20 Drawing Sheets

(56)                    References Cited

OTHER PUBLICATIONS

Kim and Hung., "An Experimental Model for Peripheral Neuropathy Produced by Segmental Spinal Nerve Ligation in the Rat," Pain, 1992, vol. 50, pp. 355-363.

Lewis et al., "Pharmacological Foundations of Cannabis Chemovars," Planta Medica, 2018, vol. 84, pp. 225-233.

Maione et al., "Non-Psychoactive Cannabinoids Modulate the Descending Pathway of Antinociception in Anaesthetized Rats Through Several Mechanisms of Action," British Journal of Pharmacology, 2011, vol. 162, pp. 584-596.

Mandolini et al., "Pharmacological Properties of Cannabidiol in the Treatment of Psychiatric Disorders: A Critical Overview," Epidemiology and Psychiatric Sciences, 2018, vol. 27(4), pp. 327-335.

Morales et al., "Molecular Targets of the Phytocannabinoids: A Complex Picture," Progress in the Chemistry of Organic Natural Products, 2017, vol. 103, pp. 103-131.

Patel et al., "The Endocannabinoid System as a Target for Novel Anxiolytic Drugs," Neuroscience Biobehavioral Reviews, May 2017, vol. 76, pp. 56-66.

Petrocellis et al., "Effects of Cannabinoids and Cannabinoid-Enriched Cannabis Extracts on TRP Channels and Endocannabinoid Metabolic Enzymes," British Journal of Pharmacology, 2011, vol. 163, pp. 1479-1494.

Russo"Taming THC: Potential Cannabis Synergy and Phytocannabinoid-Terpenoid Entourage Effects," British Journal of Pharmacology, Aug. 2011, vol. 163(7), pp. 1344-1364.

Shinjyo and Marzo., "The Effect of Cannabichromene on Adult Neural Stem/Progenitor Cells," Neurochemistry International, 2013, vol. 63(5), pp. 432-437.

U.S. Appl. No. 17/038,048, Restriction Requirement dated Jun. 10, 2022.

Wolf et al., "Cannabinoid Receptor Cb1 Mediates Baseline and Activity-induced Survival of New Neurons in Adult Hippocampal Neurogenesis," Cell Communication and Signaling, 2010, vol. 8, pp. 12.

European Patent Application No. 21792840.7, Extended European Search Report dated Apr. 11, 2024.

Korean Patent Application No. 10-2022-7040874, Korean Office Action dated Dec. 19, 2025.

Mechoulam et al., "Cannabidiol—Recent Advances," Chemistry & Biodiversity, 2007, vol. 4(8), pp. 1678-1692.

Percentage From Baseline PWT (A)

Percentage from Baseline PWT (B)

Pre-Dosing - 24 h Post-Dosing: CBC 10 mg/kg with Controls

Discriminant direction
for "Distance from BL"

CANNABICHROMENE FORMULATION FOR PAIN MANAGEMENT

CROSS REFERENCE TO RELATED APPLICATIONS

This application claims the benefit of and priority to U.S. Provisional Patent Application No. 63/015,039 filed on Apr. 24, 2020; U.S. Utility patent application Ser. No. 17/038,048 filed on Sep. 30, 2020; and U.S. Provisional Patent Application No. 63/145,040 filed on Feb. 3, 2021, the entire content of each being hereby incorporated by reference.

FIELD

The present disclosure relates generally to a formulation for medicinal use. More particularly, the present disclosure relates to a cannabinoid formulations for use in pain management.

BACKGROUND

Individuals managing pain often turn to medicinal options that offer pain alleviation, but are accompanied by unintended side-effects such as stomach upset, constipation, and risk of addiction. Alternatives to opiate drugs are urgently needed.

Cannabinoids are a group of structurally similar compounds isolated from cannabis plants, which activate cannabinoid receptors in cells. Cannabinoids may be synthesized or may be isolated from cannabis plants or plant extracts (herein: a cannabinoid-containing plant extract). Cannabinoids can be isolated from plants or extracts to the extent that they are obtained in nearly pure, or essentially pure form, free of significant amounts of other naturally occurring compounds, such as other cannabinoids or plant-derived molecules such as terpenes. Known cannabinoids include but are not limited to tetrahydrocannabinol (THC); cannabidiol (CBD), cannabichromene (CBC); tetrahydrocannabidivarin (THCV); tetrahydrocannabinolic acid (THCA); cannabigerol (CBG); cannabidivarin (CBDV), cannabinol (CBN), and cannabidiolic acid (CBDA). Cannabis plants may be bred to have different amounts of a certain cannabinoid, as may be desirable for different purposes. THC and CBD have, to date, been considered as the predominant cannabinoids of interest.

CBD has been widely studied medicinal effects. CBD is regarded as having an effect on 5HT1A receptor-mediated neurotransmission, as well as on anandamide metabolism and activation of TRPV1 receptor channels that facilitate CB1- and CB2-mediated responses (Crippa J S 2018).

$\Delta^9$-THC exerts partial agonistic activity on CB1 and CB2 receptors with high binding affinity with CB1 receptor leading to its psychoactive activity.

Cannabichromene (CBC) is a major non-psychotropic cannabinoid naturally found in the *Cannabis sativa* plant.

The proportion of each of these cannabinoids in the cannabis plant is, however, dependent on environmental growth conditions, geographical location, genetics, and chemotype (Lewis M A 2017).

CBC has moderate affinity (Ki~100 nanomolar) only for CB2 receptors and binds to CB1 receptors only at concentrations higher than 1 micromolar (Shinjyo N 2013). The major CBC activity in brain has been suggested to be partly dependent on indirect activation of CB1 receptor by inhibition of cellular uptake of anandamide (De Petrocellis L 2011) and activation of TRPA1 (Transient Receptor potential A1) channels (Izzo and Capasso R 2012). In fact, CBC is found to be the most potent agonist of all the phytocannabinoids at TRPA1 channels (Maione S 2011). CBC has also shown anti-inflammatory effects (Izzo and Capasso R 2012).

It has been demonstrated that CBD can act synergistically with $\Delta^9$-THC and contribute to the analgesic effect of medicinal-based cannabis extract (Russo 2011).

The agonistic activity of CBC with CB1 and CB2 receptors can offer a promising approach to potentiate the effect of other cannabinoids that exert their activities via binding and activation of CB1 an CB2 receptors.

Medicinal uses of cannabinoids are known, and formulations specifically to treat pain have been described. WO2007/083098 A1 (GW Pharma Ltd) describes cannabinoid-containing plant extracts for treatment of neural degeneration. U.S. Patent Publication No. US2016/0106705 (United Cannabis Corp.) describes cannabis extracts having at least four cannabinoids and a terpene or flavonoid for use in relieving anxiety, pain, and related disorders. WO2016/044370 A1 (India Globalization Capital Inc.) teaches a topical pain-relieving formulation containing a combination of THC, CBD and cobalamin. WO2013/165251 A1 (ECHO Pharmaceuticals BV) describes a thin film evaporation method for obtaining THC-containing isolates, which may have trace only amounts of CBN or CBD. In WO2012/144892 A1 (Fytagoras BV), the use of acidic cannabinoids such as THC, CBD, and other cannabinoids for enhancing an animal's natural cellular resistance to disease is described. Further, in WO2012/160358 A1 (GW Pharma Ltd.), the use of at least one of CBG, CBC, CBDV and THCV as a treatment of neuropathic pain is described.

The potential of certain individual cannabinoids to have primary medicinal effects, apart from the THC, not been fully explored. It is desirable to provide a cannabinoid formulation with beneficial properties for use in the management of pain.

SUMMARY

It is an object of the present disclosure to obviate or mitigate at least one disadvantage of previous formulations for the management and treatment of pain.

Cannabichromene has not previously been established as able to act as a primary medicinal ingredient, essentially free of THC or other well-known cannabinoids.

The formulation described herein is for use in pain management by a subject in need thereof. The formulation described herein may be for use as a medicament in a method of pain management. The formulation comprises a primary cannabinoid and an excipient, wherein the primary cannabinoid consists of cannabichromene (CBC), and the formulation is essentially free of tetrahydrocannabinol (THC).

Use of the formulation for pain management and for preparation of a medicament for pain management is described.

A commercial package comprising the formulation together with instructions for use in pain management is also described.

A method for pain management in a subject in need thereof is also described. This method comprises administering to the subject an effective amount of a formulation comprising a primary cannabinoid and an excipient, wherein said primary cannabinoid consists of cannabichromene (CBC), and wherein said formulation is essentially free of tetrahydrocannabinol (THC).

Other aspects and features of the present disclosure will become apparent to those ordinarily skilled in the art upon review of the following description of specific embodiments.

Advantageously, individuals who do not wish to consume cannabinoids such as THC due to psychoactive effects, can consume the formulation with CBC as the primary cannabinoid and still experience effective pain management.

BRIEF DESCRIPTION OF THE FIGURES

Embodiments of the present disclosure will now be described, by way of example only, with reference to the attached Figures.

FIG. 9 depicts left/right coupling, toe and tail gait variables at baseline, D7, D8-5 h, D8-9 h and D9 post-dosing. Highlighted panels represent statistically significant parameters observed upon treatment with cannabichromene for:

Toe Clearance—Hindlimb [m]; Toe Clearance—Forelimb [m]; Protraction—Hind limb [m]; and Retraction—Hind limb.

Figure 10:
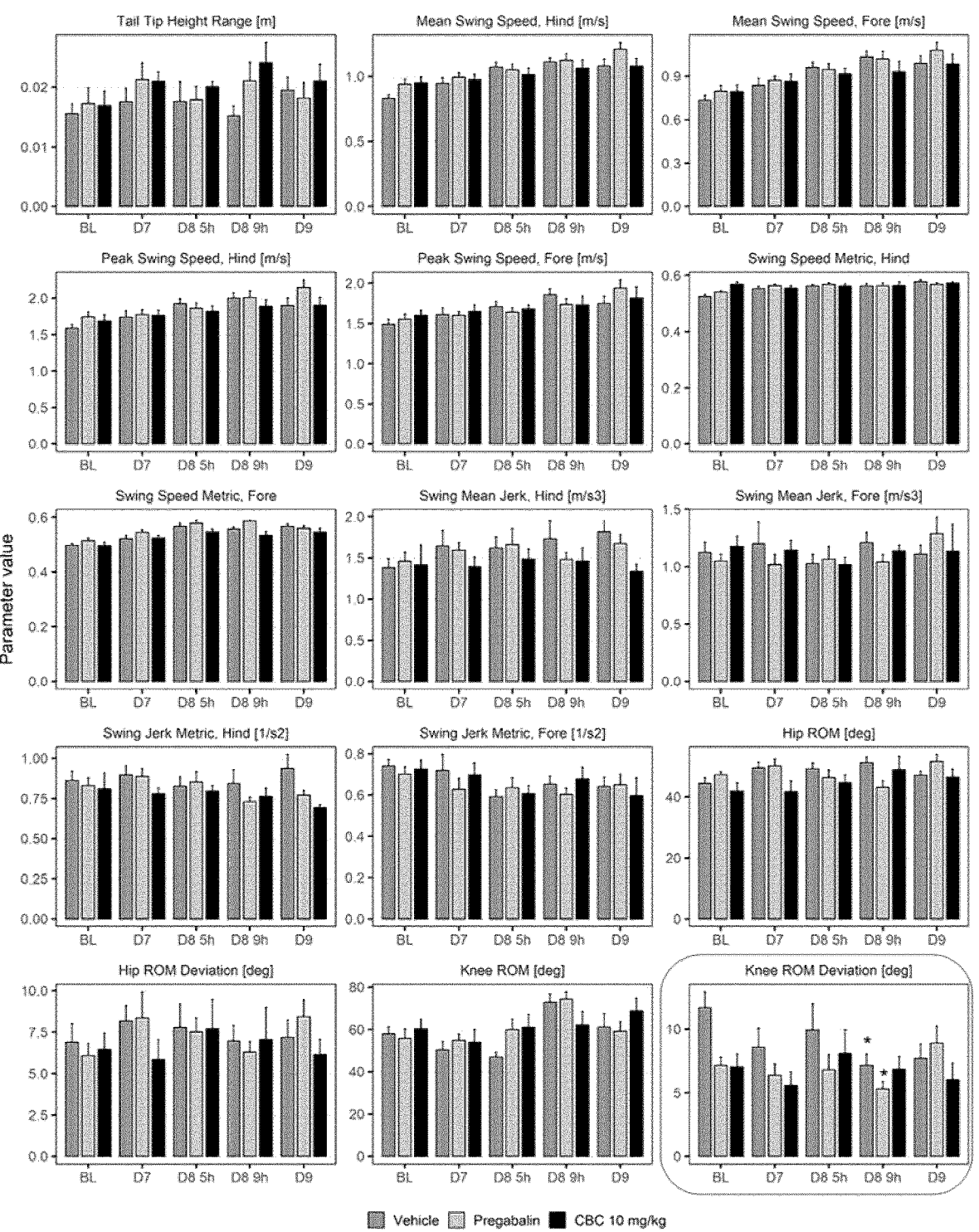

FIG. 10 depicts tail tip, swing jerk metric, hip and knee gait variables at baseline, D7, D8-5 h, D8-9 h and D9 post-dosing. Highlighted panels represent statistically significant parameters observed upon treatment with cannabichromene for Knee ROM deviation [deg].

Figure 11:
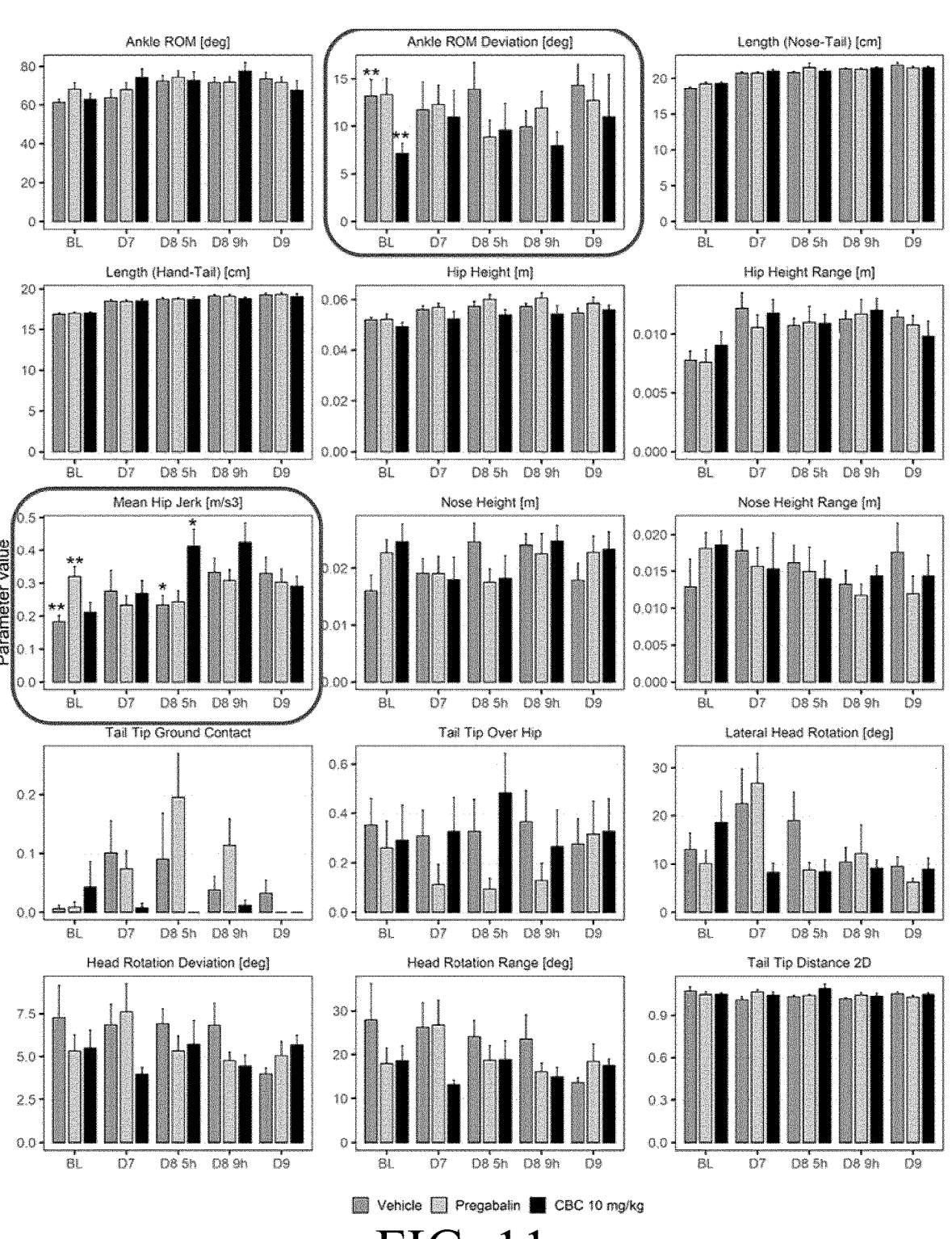

FIG. 11 depicts ankle and hip height/jerk metric, tail tip metric and head rotation gait variables at baseline, D7, D8-5 h, D8-9 h and D9 post-dosing. Highlighted panels represent statistically significant parameters observed upon treatment with cannabichromene for: Ankle ROM Deviation Degree Baseline; Mean Hip Jerk [m/s$^3$]; and Mean Hip Jerk [m/s$^3$].

Figure 12:
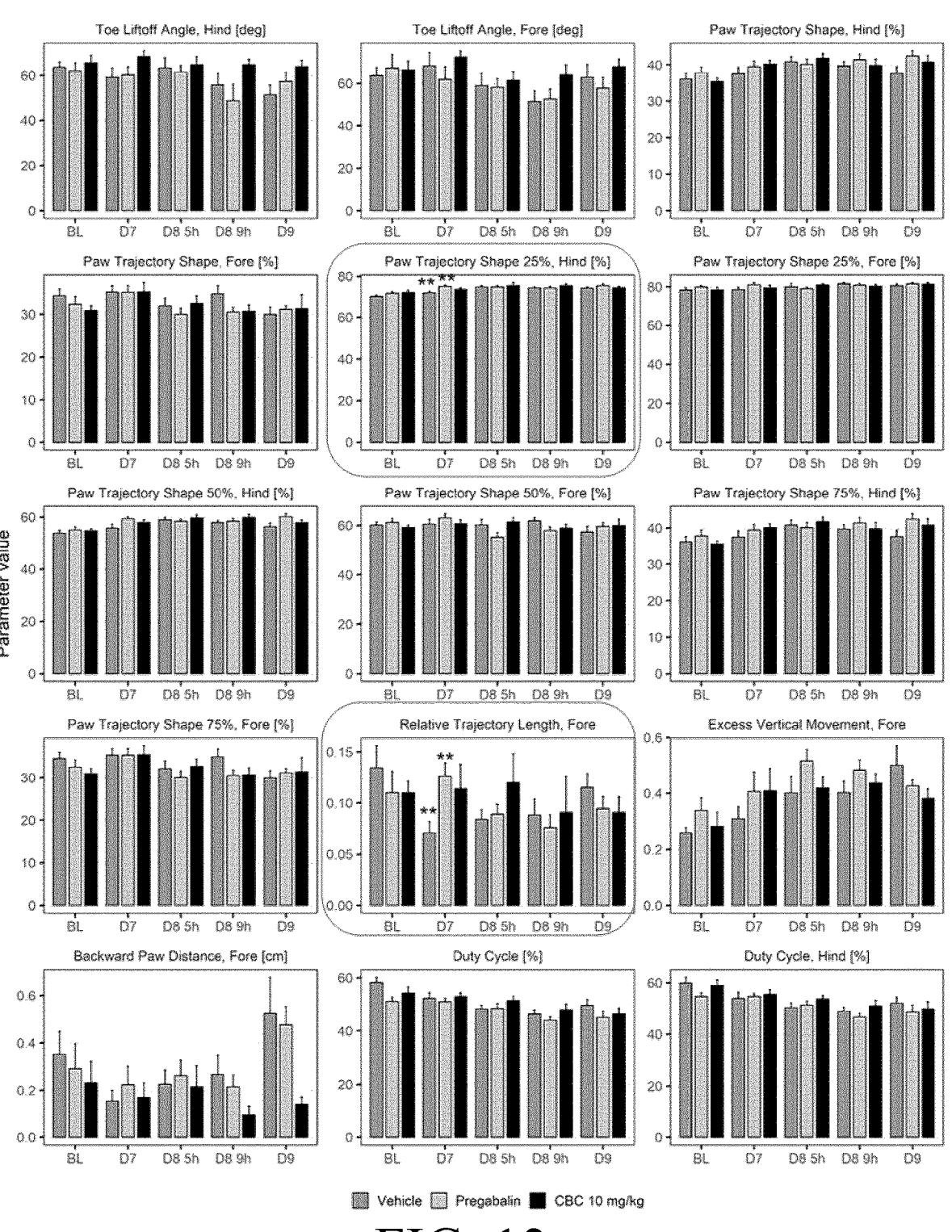

FIG. 12 depicts toe lift, paw trajectory metric, paw distance and duty cycle gait variables at baseline, D7, D8-5 h, D8-9 h and D9 post-dosing. Highlighted panels represent statistically significant parameters observed upon treatment with cannabichromene for: Paw Trajectory Shape 25%, Hind limb [%]; and Relative Trajectory Length, Forelimb.

Figure 13:
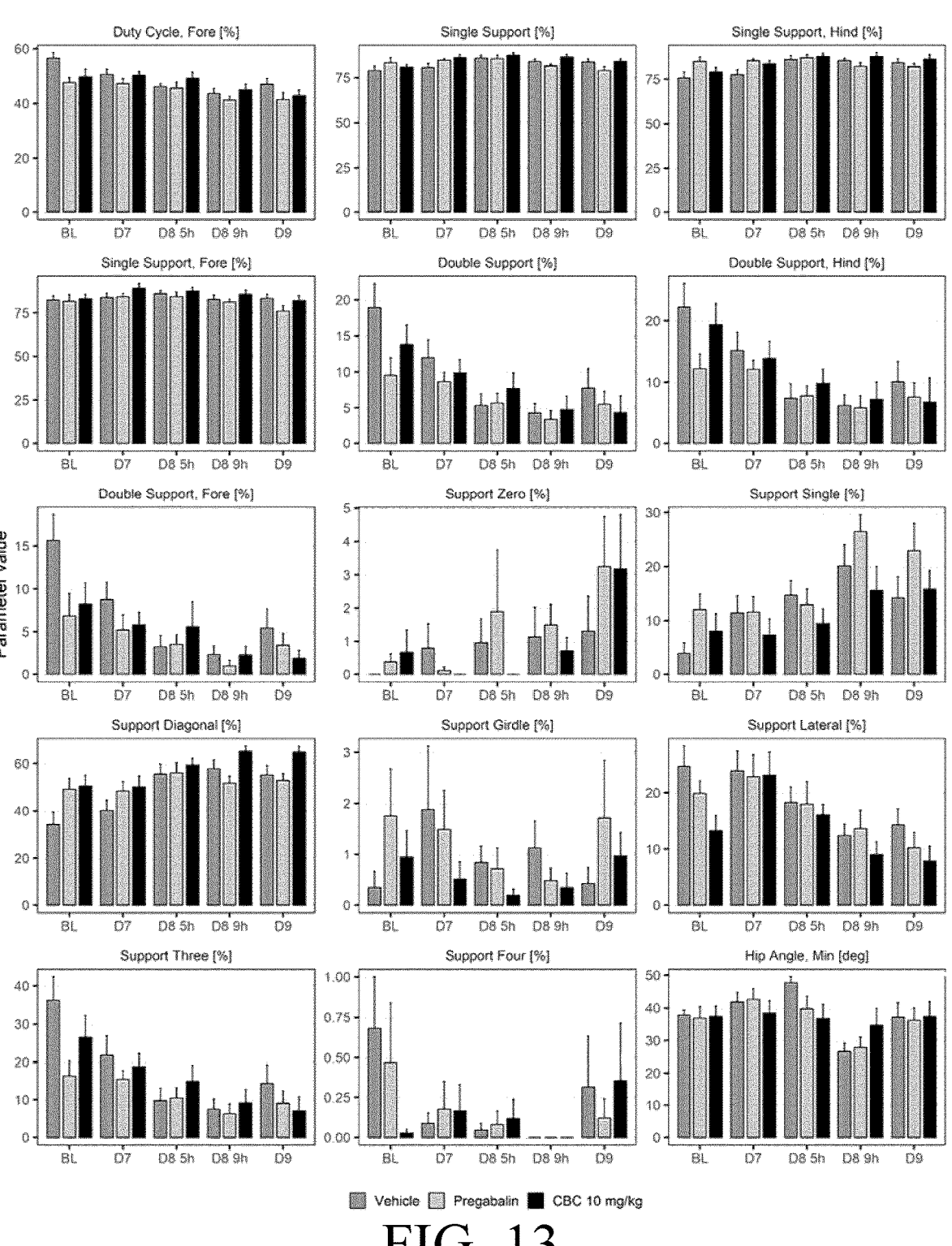

FIG. 13 shows support metric gait variables at baseline, D7, D8-5 h, D8-9 h and D9 post-dosing. The absence of highlighted panels indicates no statistically significant parameters observed upon treatment with cannabichromene in support metric of mice treated with cannabichromene compared to vehicle.

Figure 14:
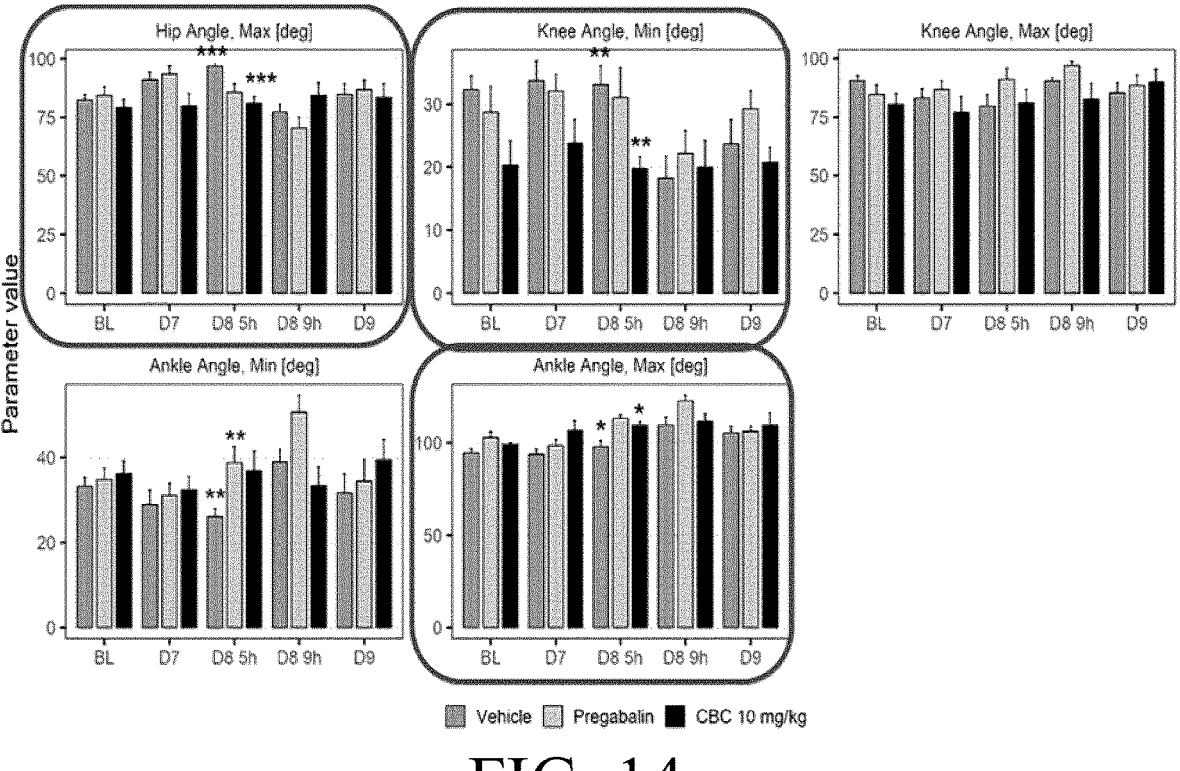

FIG. 14 depicts hip, knee, and ankle angle gait variables at baseline, D7, D8-5 h, D8-9 h and D9 post-dosing. Highlighted panels represent statistically significant parameters observed upon treatment with cannabichromene for: Hip Angle, Max degree; Knee Angle, Min Degree; Ankle Angle, Min degree; and Ankle Angle, Max degree.

Figure 15:
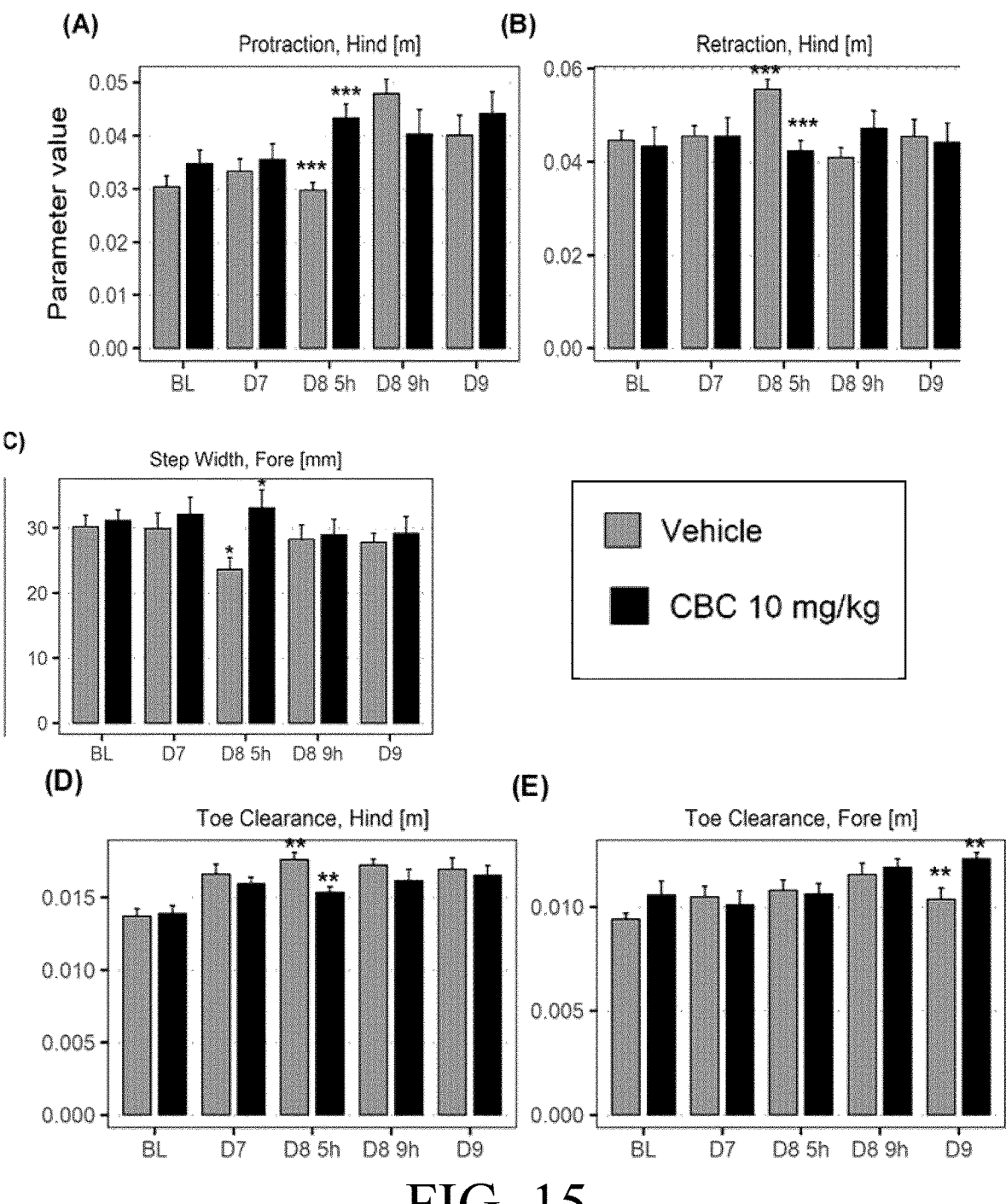

FIG. 15 shows protraction, retraction and toe clearance and step width gait variables at baseline, D7, D8-5 h, D8-9 h and D9 post-dosing in CBC treatment vs. vehicle. Panel A shows Protraction: Hindlimb; Panel B shows Retraction: Hindlimb; Panel C shows Step Width: Forelimb; Panel D shows Toe Clearance Hindlimb; and Panel E shows Toe Clearance Forelimb [m].

Figure 16:
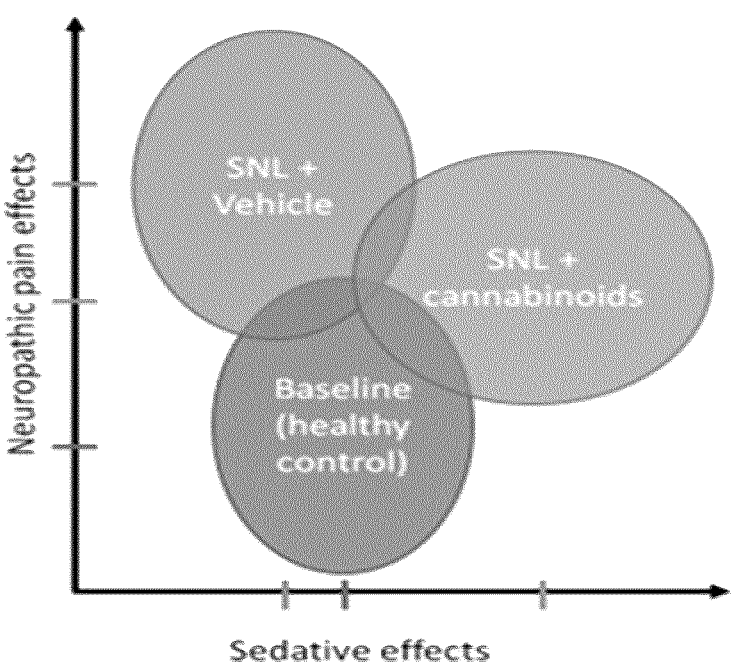

FIG. 16 models the neuropathic pain effects versus sedative effects on different axes. Cannabinoid groups may demonstrate treatment effects in the pain axis (Y-axis), while simultaneously, there might be a change in sedative effects (X-axis).

Figure 17:
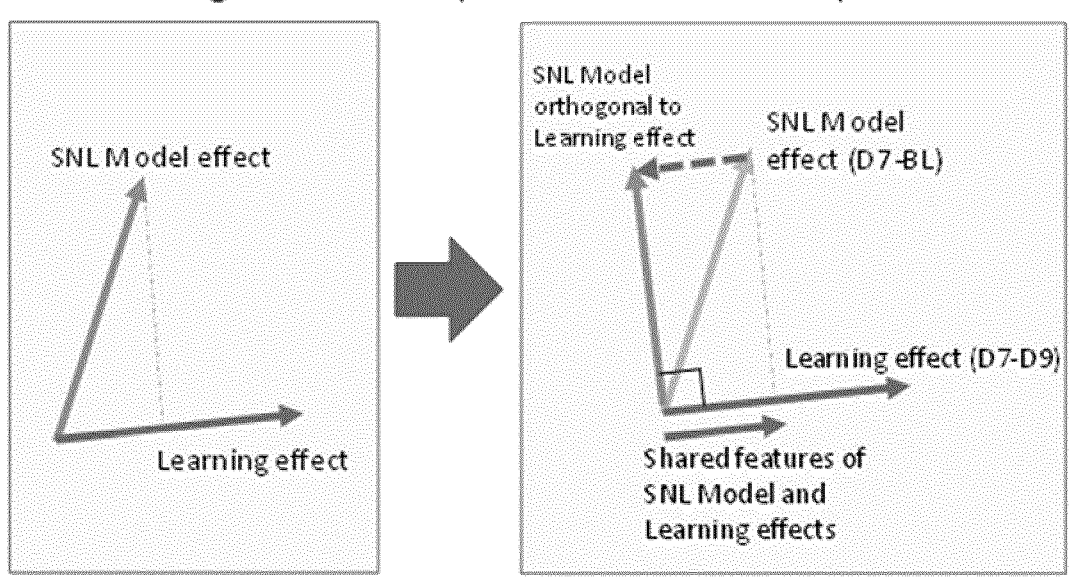

FIG. 17 shows an orthogonalization process of two components: SNL model effect and learning effect.

Figure 18:
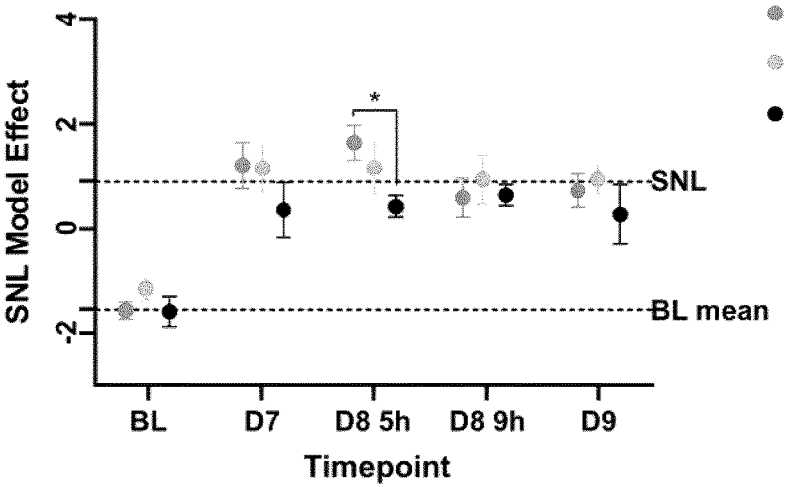

FIG. 18 shows the final analgesic effect of CBC from 0 to 24 hours post-treatment. Data is analyzed based on SNL model effects orthogonalized against the learning effect.

Figure 19:
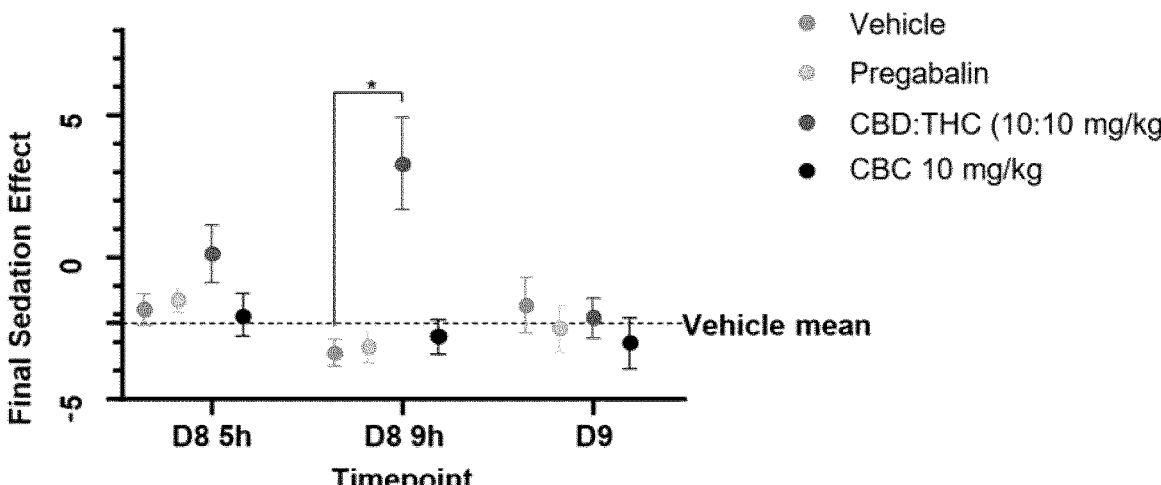

FIG. 19 shows that sedation effect is orthogonal to the model effect. The final independent sedation effect scores, orthogonal to both SNL model and learning effects.

Figure 20:
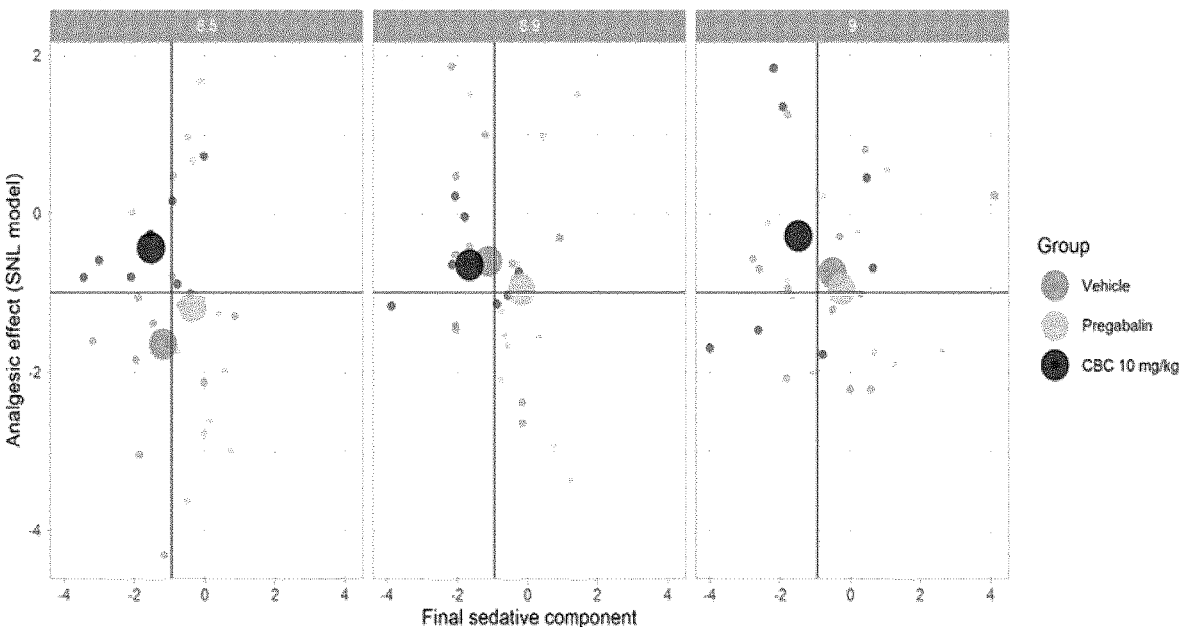

FIG. 20 shows the analgesic vs. sedative effect scores of CBC, which are presented as XY-plot based on the steps averaged gait parameter at 5-24 hours post-treatment.

Figure 21:
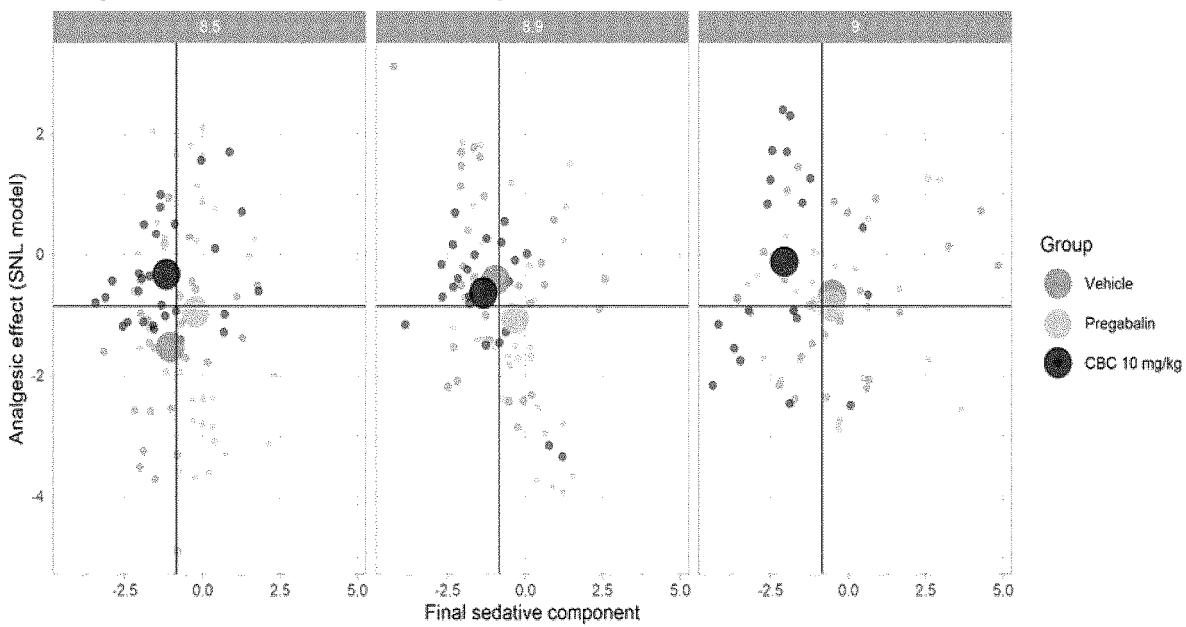

FIG. 21 shows analgesic vs. sedative effect scores of CBC, presented as XY-plot based on the individual steps gait parameter at 5-24 hours post-dosing.

Figure 22:
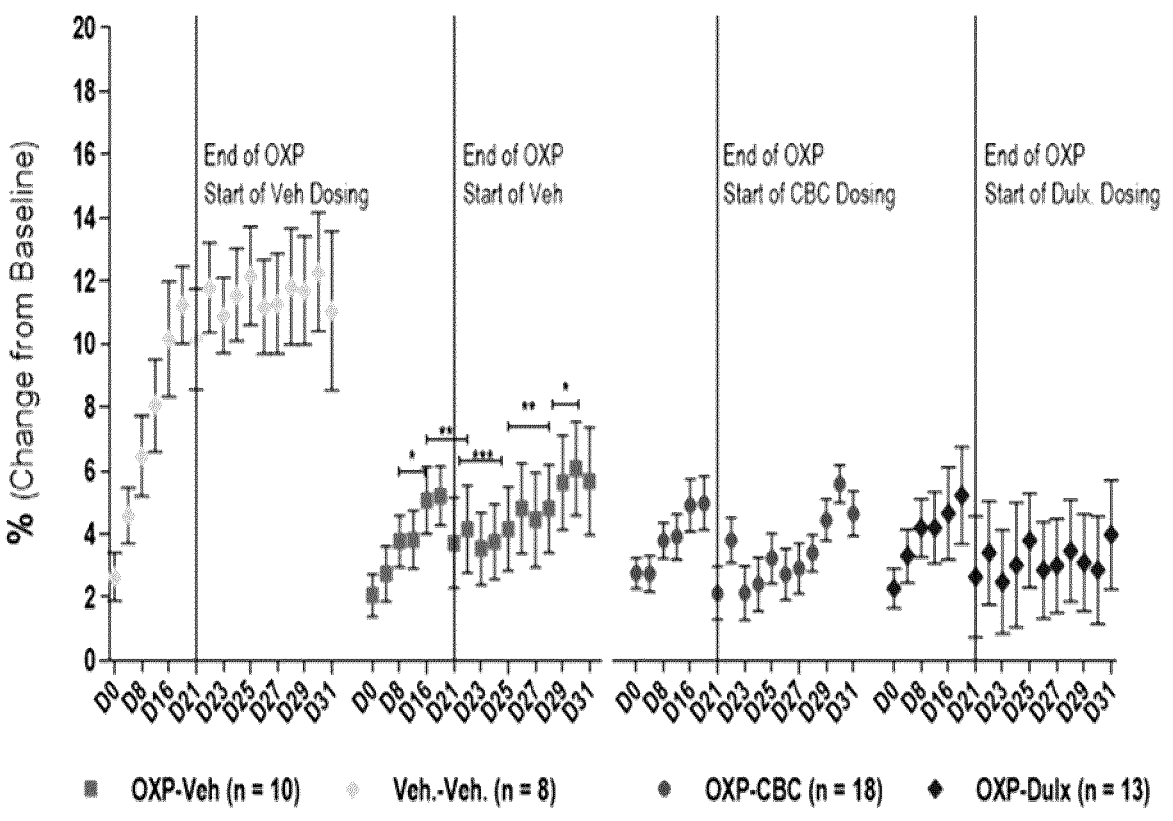

FIG. 22 shows body weight development presented as Mean % BW change from baseline for Example 5. Data are presented as mean±SEM.

Figure 23:
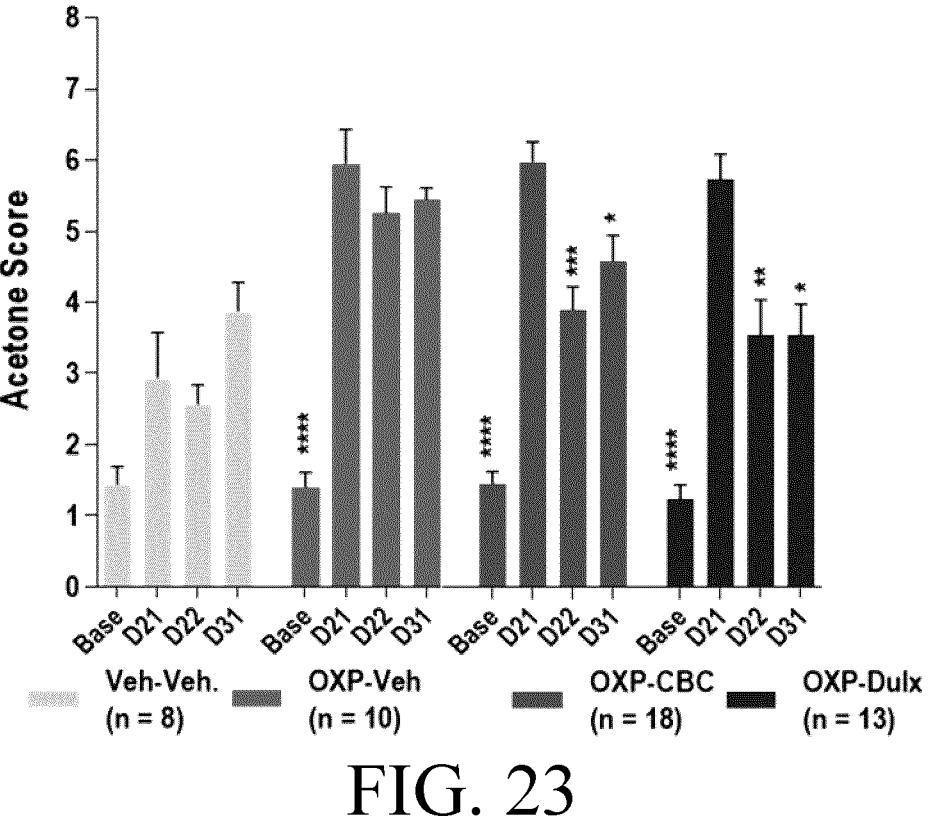

FIG. 23 shows a within treatment group comparison of mean ACT scores at indicated timepoints for Example 5.

Figure 24:
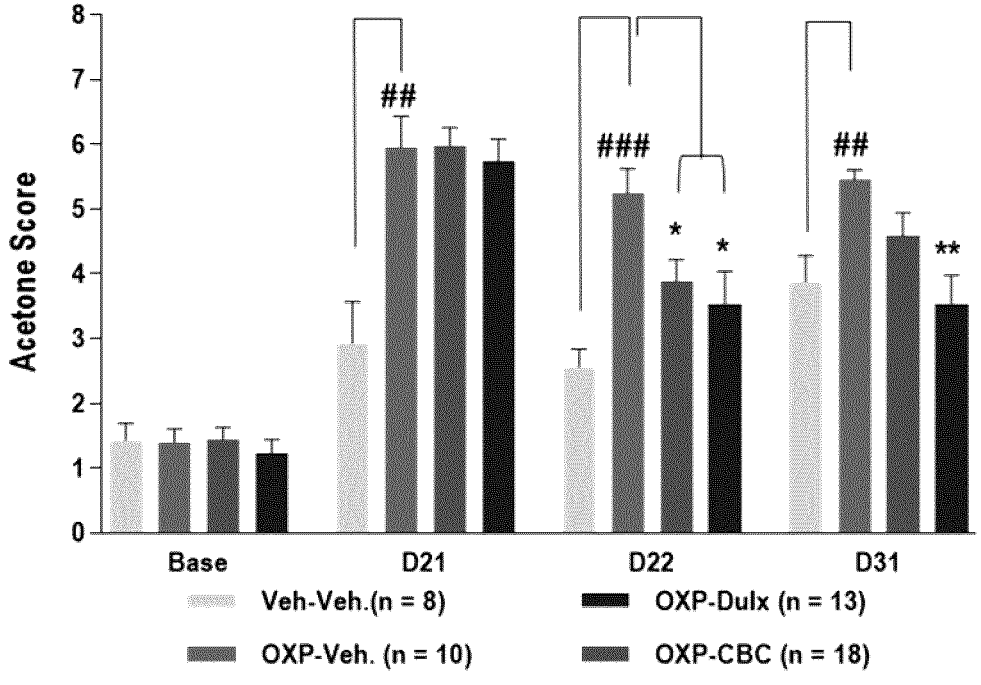

FIG. 24 shows a between treatment group comparison of mean ACT scores at indicated timepoints for Example 5.

DETAILED DESCRIPTION

Generally, the present disclosure provides a cannabichromene formulation for pain management, and method for managing pain. It has not previously been recognized that cannabichromene can have an effect on pain management when relied upon as the primary cannabinoid in a formulation.

A formulation for use in pain management by a subject in need thereof is described. The formulation comprises a primary cannabinoid and an excipient. The primary cannabinoid consists of cannabichromene (CBC). The formulation is essentially free of tetrahydrocannabinol (THC), meaning that small and insignificant amount may be present, for example at an amount of 2% or less by weight of the CBC. The management of pain attributable to the singular presence of the CBC as the primary cannabinoid in the formulation has been surprisingly found.

A formulation is described herein for use in a method of pain management by a subject in need thereof, said formulation comprising a primary cannabinoid and an excipient, wherein said primary cannabinoid consists of cannabichromene (CBC), and wherein said formulation is essentially free of tetrahydrocannabinol (THC). Essentially free may mean an insignificant amount, for example at 2% by weight or less, 1% by weight or less, 0.5% by weight or less, or 0.1% by weight or less as compared with the weight of the primary cannabinoid.

The formulation may be used to treat pain due to neuropathic pain, cancer, chemotherapy, inflammation, diabetes, diabetic neuropathy, post-shingles neuralgia, peripheral neuropathy, multiple sclerosis, injury, accident, surgery, or tissue damage.

The formulation may additionally comprise one or more secondary cannabinoids, preferably cannabidiol (CBD).

The formulation may comprise the one or more secondary cannabinoids in an amount of up to 15% by weight of the primary cannabinoid.

The formulation may be prepared in a dosage form selected from the group consisting of a pill, tablet, gel capsule, syrup, oil-based spray, and liquid oil form.

The formulation may provide a total amount of from about 1 mg to about 25 mg of primary cannabinoid per dose, preferably from about 5 mg to about 20 mg.

A use of the formulation for pain management in a subject in need thereof, or use for preparation of a medicament for such pain management is described herein.

A commercial package is described herein, comprising the formulation together with instructions for use in pain management.

A method for pain management is described herein for use by a subject in need thereof, comprising administering to said subject an effective amount of a formulation comprising a primary cannabinoid and an excipient, wherein said primary cannabinoid consists of cannabichromene (CBC), and wherein said formulation is essentially free of tetrahydrocannabinol (THC).

The pain to be managed in the method may comprise alleviating pain due to neuropathic pain, cancer, chemotherapy, inflammation, diabetes, diabetic neuropathy, post-shingles neuralgia, peripheral neuropathy, multiple sclerosis, injury, accident, surgery, or tissue damage.

In the method described, the formulation may additionally comprise one or more secondary cannabinoids, preferably cannabidiol (CBD).

The formulation used in the method may involve the one or more secondary cannabinoids being present in the formulation in an amount of up to 15% by weight of the primary cannabinoid. The method may involve administration in a dosage form selected from the group consisting of a pill, tablet, gel capsule, syrup, oil-based spray, and liquid oil form.

The method may comprise administration to the subject an amount of the formulation that provides to the subject a total amount of from about 1 mg to about 25 mg of primary cannabinoid per dose, preferably from about 5 mg to about 20 mg per dose.

Primary Cannabinoid. The term "primary" is meant to indicate the cannabinoid that is primarily responsible for the intended effect of pain management, as described herein. CBC is the primary cannabinoid, and it has been surprisingly found to be effective when used without significant amounts of other cannabinoids in the context of pain management. If another cannabinoid is present in the formulation in a lower amount, the quantity present would not render it a "primary" cannabinoid. But other cannabinoids can be present in the formulation as secondary cannabinoids.

Cannabinoid Sources. The primary cannabinoid, CBC, may be present in the formulation from natural sources, such as from one or more cannabis plants, an in particular extracts thereof. Or the primary cannabinoid may be obtained from one or more isolated sources, or from a synthetic source where one or more of the desired cannabinoids is synthesized. A blend of natural and synthetic cannabinoids may be used so that a natural source with a variable content (due to growing conditions or other reasons), may be standardized to pre-determined amounts using adjustment with synthetic or isolated sources.

An extract may be obtained from a plant that is specially modified or grown under conditions conducive to production of a cannabinoid ratio particularly suited to the desired primary cannabinoid ratio, without needing to dramatically alter or supplement the amount of any of the primary cannabinoids present.

If purification of cannabinoids is desired extraction methods such as an ethanolic extraction, or a $CO_2$ based extraction may be used.

Cannabinoids may be incidentally present in the formulation, and if present, the quantities of such additional cannabinoid ingredients would not reduce or significantly influence the pain management features of the formulation.

Pain Management. The intended use of this formulation for pain management may include cancer-related pain as well as neuropathic pain, pain caused by cancer, or non-cancer-related pain, pain associated with inflammation, acute pain from injury, accident, surgery, or from tissue-damaging conditions such as arthritis and joint pain, pain from infections, from gastrointestinal-derived pain, or from other sources of pain.

Subjects and Populations. The formulation may be used by humans or by pets (companion animals such as dogs or cats), as well as for working animals such as horses.

Subjects in need of a therapeutic effect for pain management in the intended indications may use the formulation prior to, during, or after the medical event or need arises. Cancer pain can be debilitating for a number of reasons, and cancer treatments can also lead to painful episodes. Management with the formulation described herein can avoid problems inherent with opiate use, such as constipation and addiction. Addition can lead to overuse, and eventually illegal sourcing of formulations that are unpredictable in composition, which may lead to overdose.

Regarding non-cancer pain, for example, prior to undergoing surgery where the pain can generally be anticipated, the formulation may be used prophylactically to lessen the pain that is anticipated. For the pain of an injury or unexpected damage from an accident, the formulation may be used acutely or on an ongoing basis in place or harsher or more damaging analgesic drugs such as opioids or NSAID pain killers.

Mode and Forms of Delivery. The formulation is amenable to oral delivery, such as in a pill, tablet, gel capsules, syrup, oil-based spray, or liquid oil form. The oral form may be provided in a food or as a food supplement, which may be added to a food to be more palatable or readily consumed by a subject. Topical or nasal absorption is possible. A fat-soluble carrier, or nano- or micro-particles or emulsions may be used so that the highly fat-soluble cannabinoids can be more readily absorbed. The formulation may be prepared as an injectable, for intravenous, intramuscular, or intraocular delivery. The formulation may be delivered in a vapor, such as by vaping, in a vaporizer or puffer, or may be heated to cause volatilization and inhalation which could be considered as "smoking".

Dosages. CBC is the primary cannabinoid in the dosage form of the formula. Other cannabinoids may be present in the formulation. On a per dosage basis, the total amount of primary cannabinoid may range from 0.1 mg-50 mg, for example 1 mg-25 mg, or 5 mg-20 mg per dose. If delivered in a liquid such as an oil, amounts may be expressed on a mg/mL basis, such as from 0.1 mg/mL-50 mg/mL per dose, for example 1 mg/mL-25 mg/mL, or 5 mg/mL-20 mg/mL per dose. Dosages may be used as needed depending on the severity of the pain experienced, but an individual may wish to use the formulation on an as-needed basis, ranging from once per day (or less, if not needed) to more frequently such as taking 6 doses per day, with a frequency of every 4 hours.

An exemplary formulation may be a solid dosage form such as a pill, tablet, or granule-containing capsule. Alternatively, the formulation may be liquid-based, and may contain isolated or synthetic primary cannabinoid, or may be an oil-based extract of cannabis with significant quantities of CBC. The formulation may be in liquid forms such as oil, and oil-based spray, or a liquid-containing gel capsule (soft-gel capsule). If liquid-containing or gel-containing capsules are used, these may be limited in volume, for example an approximate volume of 200 µL. The milligram quantity stated above as a dosage range may be included in each such capsule, or the capsules may be formulated so as to be less concentrated in units of mg/mL. When less concentrated capsules are used, then the appropriate dosage is delivered by increasing the number of capsules consumed per dose.

Excipients and Formulation Ingredients. The formulation may incorporate any acceptable excipients known in formulating drugs or cannabinoids. Such ingredients may include starch, cellulose, alginates, colloidal silicon, lubricants such as stearates, salts, aqueous and non-aqueous (fat soluble) ingredients. The usual formulation considerations would be brought to bear, as one of skill in the art would understand.

Example 1

Formulation for Use in Inflammatory Pain Management

The pain that accompanies inflammation is highly variable depending on the underlying cause. Inflammatory pain that may be attributed to increased excitability of peripheral nociceptive sensory fibres can be addressed by the present formulation. The altered activity of ion channels in sensory neurons, causing pain, can be lessened. This can address a number of conditions associated with chronic inflammation.

An individual with inflammatory pain may consume orally, on a regular basis such as every 6-hours, a dose of the following oil-based cannabinoid formulation.

The formulation comprises 20 mg/mL CBC, and 1 mg/mL CBD, in an oil-based liquid. At the appropriate interval, the individual may take 1 mL orally.

Initially, the individual may begin by consuming 1 mL of the formulation at a frequency of twice per day. The dose may be titrated to a higher amount over time as the individual becomes accustomed to the formulation, until a dose of 1 to 2 mL, taken from 4 to 6 times per day is reached.

Example 2

Formulation for Managing Pain Due to Injury

The pain accompanying an acute and unexpected accident or injury can be debilitating to the individual, slowing the process of therapy and recovery.

An individual experiencing acute pain brought on by injury may use the formulation to manage this pain. Then individual may consume orally, on a regular or as-needed basis, a dose of the following encapsulated oil-based cannabinoid formulation until the pain subsides to a tolerable level.

The formulation is present in soft-gel capsules having an approximate volume of 200 µL per capsule. Each capsule comprises 10 mg CBC in an oil-based liquid. The soft-gel capsule encapsulates the oil-based liquid with a gelatin-based shell that may incorporate other commonly known gel capsule ingredients, such as glycerin or sorbitol, permitting easy swallowing. At the appropriate interval, the individual may take 1 capsule orally.

The individual may consuming 1-4 capsules at a frequency of 2 to 4 times per day. The dose may be increased to a higher amount if the dose is well tolerated, and as the individual becomes accustomed to the formulation. Over time, as the individual recovers from the injury and the pain is lessened the frequency of use may be titrated down to a dose of 1 capsule twice per day, or less frequently is used on an as-needed basis.

Example 3

Pain Management in Neuropathic Pain

ABSTRACT. A formulation for pain management is described for use by individuals experiencing pain. The formulation comprises cannabichromene in optimized amounts to manage pain. An excipient, diluent or carrier is included in the formulation. The types of pain that can be managed with the formulation include but are not limited to the treatment of pain due to inflammation, chemotherapy, cancer, diabetes, injury, accident, surgery, or tissue damage. The Spinal Nerve Ligation (SNL) Model is an appropriate animal system in which to study pain such as from multiple sclerosis (MS), diabetic neuropathy, post-shingles neuralgia, or peripheral neuropathy (widespread nerve damage). This Example illustrates efficacy in an animal model of pain of this cannabichromene formulation. Significant and highly significant reversion of tactile allodyia and improvement of SNL-induced functional performance were produced by cannabichromene. Cannabichromene displayed higher efficacy on tactile allodynia, than the reference analgesic (Pregabalin, 50 mg/kg). In summary, cannabichromene illustrated a highly potent analgesic effect, suitable for use in pain management. Gait analysis results revealed that cannabichromene can ameliorate motor neuropathy, absent significant contributing effects of other cannabinoids such as CBD and THC.

INTRODUCTION. A large proportion of the global the population is affected by pain. Safe and effective treatment for pain is desirable. The objective of this study was to evaluate the effect of cannabichromene (CBC) Spinal nerve ligation (SNL)-induced mechanical hypersensitivity and altered kinematic performance. The SNL-induced model is indicative of the effect of cannabichromene on pain relief. Gait analysis and other parameters showed a significant improvement in mechanical hypersensitivity and kinematic performance in the treatment group receiving cannabichromene at 10 mg/kg. The reduction in mechanical hypersensitivity improved kinematic performance of SNL-induced neuropathic pain. The improvement was shown as compared a control vehicle, as well as compared with the analgesic effect of pregabalin, a GABA (gamma aminobutyric acid) analogue that is among current treatment choices.

Cannabichromene can be effective as the sole ingredient in a formulation providing analgesic effect without the need for other cannabinoids to be present in significant amounts. Formulations comprising CBC enable the possibility of a significant reduction in the use of pain relieving drugs associated with problematic effects, such as opioids.

PURPOSE OF THE STUDY. The objective of this study was to evaluate the effect of cannabichromene (CBC) treatment on spinal nerve ligation (SNL)-induced mechanical hypersensitivity and altered kinematic performance.

Spinal nerve ligation surgery causes partial denervation within the peripheral (sciatic) nerve, thereby evoking tactile hypersensitivity (allodynia) within the sciatic nerve innervation area. The SNL rat model was originally described in 1992 (Kim S H et al., 1992), and is performed by placing tight ligatures onto the L4 and L5 spinal nerves. Neuropathic pain may affect several aspects of quality of life in up to 10% of all people worldwide (Colloca et al., 2017). Effective and safe treatments for neuropathic pain are needed. Cannabinoids possess several functions according to their reactions with the endocannabinoid system. Cannabichromene is a promising candidate for use in alleviating different pain types. Previously, cannabichromene was considered to be incidentally present in plant-based pain-relieving formulations, with the focus being largely on CBD and THC combinations.

The study protocol was conducted via the following steps:

D −7 to D −1: Prior to surgery, baseline test for tactile allodynia (mechanical sensitivity of the naïve rats) by electronic von Frey test (evF); baseline gait analysis.

D0: Spinal nerve ligation surgery.

D0 to D6: Post-operative care period.

D7: evF and gait analysis, to define the injury baseline allodynia and SNL-induced changes in motor performance (respectively). D7 tests also defined the pre-dosing sensitivity and—motor performance D8: At 0 h: administration of cannabichromene or pregabalin; evF at 2 h, 4 h, and 8 h post-dosing (PD); gait analysis at 5 h and 9 h PD.

D9: evF test at 24 h PD. After the final tests on D9, part of each group was euthanized.

D10 (the remaining rats): At 0 h: administration of cannabichromene or pregabalin; At 2 h, 4 h, and 8 h PD: PK plasma sampling.

D 11: 24-h PK plasma sampling upon euthanization, along with sampling of brain and lumbar DRGs.

Materials and Methods

Test Formulation. The test formulation was delivered to Charles River Laboratories Discovery Services (CRL DS)

by Purisys Advanced Cannabinoids (Athens GA, USA). The test formulation was handled and stored and the dose formulation prepared according to detailed instructions provided by the Vendor.

Equipment, Reagents and Solutions. The following materials and substances were used in the study: Steel mesh test plane: Ugo Basile, Germany. Plexiglass test chambers: Ugo Basile, Germany. Electronic von Frey test hard- and software: Somedic, Sweden. MotoRater: TSE Systems, Homburg, Germany. Gas anesthesia equipment: Harvard Apparatus. Isoflurane liquid: Attane Vet. Light Microscope: Zeiss Stereomicroscope, Stemi DV4. Homeothermic surgery blanket thermostat and probe: Harvard Apparatus. Silk Suture for the ligatures: 6-0 Ethicon. Polyamide suture (5-0): Ethicon. Buprenorphine Temgesic®: Oriola Finland. 0.9% NaCl (Saline): Braun.

Test Animals. All animal experiments were performed as specified in the license authorized by the national Animal Experiment Board of Finland and according to the National Institutes of Health (Bethesda, MD, USA) guidelines for the care and use of laboratory animals. 226 male Sprague-Dawley male rats were purchased from Charles River Germany, to attain appropriate group sizes, due to a high percentage of animals manifesting mild or no mechanical hypersensitivity.

The body weight of the rats was 200-300 g on the day of SNL operation. Animals were housed at standard temperature (22±1° C.) and in light-controlled environment (lights on from 7 am to 8 pm) with ad libitum access to food and water.

All animals were operated by spinal nerve ligation (SNL); the group size was planned to be of n=15. After the unexpectedly high number of exclusions, the final group sizes were n=7-12.

The treatment groups received the following test article mixtures:

Group 1: treated with vehicle (0.9% saline)

Group 2: treated with Pregabalin (50 mg/kg)

Group 3: treated with CBC (10 mg/kg)

All rats followed the same study design until completion of the D9 behavioral tests.

Six rats from each group formed PK groups, which received second doses of the corresponding test articles on Day 10, followed by PK-plasma sampling. The endpoint samples were collected from these rats only.

Administration of Treatments. CBC (cannabichromene) formulation, the vehicle, or pregabalin treatment was administered according to Table 1 on study day 8 to all study animals, and on study day 10 to 6 animals per group. The dousing route of CBC or the vehicle were intragastric (p.o.), while pregabalin was administered intraperitoneally (i.p.). In addition to D8, pregabalin was administered on D9, at 2 h prior to the evf test. All animals of the pregabalin group were euthanized on D9, following the last test trial. The CBC was dissolved and diluted to one of the following vehicles:

Vehicle 1: 15 mg/mL corn oil, 10% Ethanol, 5% Kolliphor HS in Saline (used for vehicle-administrations, diluting CBC).

Vehicle 3: 500 mg/mL corn oil, 10% Ethanol, 5% Kolliphor HS in Saline used for the final formulations (in order to bring the oil concentration of all formulations to the same level).

Table 1 shows treatments groups with test articles (CBC), pregabalin and vehicle used in this example.

TABLE 1

| Group | n | Pregabalin (mg/kg) | CBD (mg/kg) | CBC (mg/kg) | THC (mg/kg) | Vehicle | Doses/ Rat | evF Test | MR Test |
|---|---|---|---|---|---|---|---|---|---|
| | | | | | | Compound Doses and treatment Group Inrmation for the Behavioural Study Phase (D 0-D 9) | | | |
| 1 | 15 | 0 | 0 | 0 | 0 | | 1 | BL, D 7, D 8 | BL, D 7, D 8 |
| 2 | | 50 | 0 | 0 | 0 | Saline | 2 | (3 timepoints), | (2 timepoints), |
| 3 | | 0 | 0 | 10 | 0 | Corn oil; 10% EtOH; 5% Kolliphor | 1 | D 9 | D 9 |

Spinal Nerve Ligation (SNL) Surgery. The animals were enrolled to SNL surgery in daily cohorts of n=6, according to the number of animals operated per day). The rat first received an intraperitoneal dose of 0.03 mg/kg buprenorphine (Temgesic), at minimum of 30 minutes prior to the surgery, to alleviate the operative and postoperative pain unrelated to neuropathy. The rats were anesthetized with isoflurane in 70% $N_2O$ and 30% $O_2$; with a flow rate of 300 ml/min. Anesthesia was inducted with 5% isoflurane for 2-3 min, and maintained through a snout mask with 1-2% isoflurane thereafter.

A dorsal incision extending from L3 to S2 was performed to the medial dorsal area of the rat using aseptic technique. The L6/S1 posterior intrarticular process was exposed using a combination of blunt and sharp dissection. The L6 transverse process in the spinal column was visualized and partially removed without manipulating the nerves, followed by exposing the L4 and L5 spinal nerves distal to their emergence from the intervertebral foramina. Tight double knots of 6-0 silk suture were placed on both spinal nerves.

After performing the ligatures, the tissue layers and wound were closed and animals allowed to recover from anesthesia in a homeothermic cage.

Postoperative care period occurred twice-daily for ad 7 days following surgery, and included the following procedures:

Careful observation of the general condition and welfare along with monitoring the operated paw and gait of the animal.

The surgical wound and sutures were checked—and disinfected properly when required—twice a day, until the wound was properly closed.

0.03 mg/kg of buprenorphine s.c. was administered upon first two postoperative days, at approximately every 12 hours.

Rehydration with 4 ml of sterile saline i.p. directly after the surgery, continuing twice a day ad 7 days, or until no further weight loss occurred.

Tactile Allodynia Test (evF). In this study, mechanical sensitivity to punctate stimulus was defined at six time points, by using electronic von Frey (evF) device with the attached analysis software (Somedic®, Sweden).

Before the baseline evF, rats were pre-handled for 2-3 min, on two consecutive days, in purpose of decreasing startling-based oversensitivity in the test. Pre-handling was performed at a maximum of 3 days prior to baseline tests.

Rats displaying inborn oversensitivity were disqualified from the study. Oversensitivity was defined as baseline paw withdrawal threshold (PWT) of <20 g with 1 mm probe. Following the baseline evF testing, the rats were weighed and numbered prior to surgery.

To perform the evF test, the rats were placed in individual von Frey test chambers standing on an elevated steel mesh. The rats were allowed to adapt in the chambers, and the test emerged after they had settled down after investigating the chamber and grooming (approximately 15 min).

Mechanical allodynia was assessed by evF test prior to SNL surgery (baseline), to define the individual "innate" sensitivity levels of the study animals. Next, the evF was performed on D7 post-SNL, to assess the hypersensitivity evoked by the SNL surgery, and to evaluate pre-dosing sensitivity values. Next day (D8), the animals were tested by evF at 2 h, at 4 h, and at 8 h post-dosing (PD). The last evF time point occurred at 24 h PD, i.e. on D9. The listed post-dosing times were used for all groups except group 2, which on D9 received pregabalin at 2 h prior to evF.

The evF apparatus was used according to the manufacturer's instructions. Briefly, upon each measurement, the force was applied to mid-plantar surface of the hind paw in a linearly increasing rate. The used evF probe diameter was 1 mm, and the chosen ascent rate of force 10 g/s. Linearity of force application was monitored real-time. The applied force (in grams) causing paw withdrawal was recorded by the Notes were taken during the test so, that any possible sedative effects of the test articles were captured by recording.

Altogether 5 repeated measurements were applied to each hind paw at each time-point, leaving a minimum of 3-min interval between the repeats. Three values closest to the median were then averaged to produce result value for each paw at any given time point. Both ipsi- and contralateral paws were tested on each test day.

Fine Motor Kinematic Gait Analysis. The subjected to gait analysis at the baseline and on study days 8, 9, 11, 14 and 17, at a minimum of 30 min after the evF test. The assay was carried out by MotoRater (TSE Systems, Homburg, Germany), with the walking mode. Prior to commencing the test, the essential body points (e.g. joints, limbs, nose, tail) were marked for tracking. The information of the gait performance was captured using a high speed camera (300 frames/second) from below and both sides. Next, the captured videos are converted to custom software. The raw data was obtained by tracking the marked points of the body from the videos recorded from all 3 dimensions. The raw data thus comprise correlation of the movements of different body points in coordinates related to the ground and each three dimensions.

Different gait patterns and movements were analyzed using a custom made automated analysis system. Information about altogether over a hundred kinematic parameters were attained. These comprised e.g:

General gait pattern parameters such as: stride time and—speed, step width, stance and swing time during a stride, and interlimb coordination.

Body posture and balance parameters, such as: toe clearance, iliac crest and hip height, hind limb protraction and retraction, tail position and movement.

Fine motor skills, including e.g. the swing speed during a stride, jerk metric during swing phase, angle ranges and deviations of different joints, and vertical plus horizontal head movements All MotoRater data were analyzed for the distinct parameters, as well as for all combined parameters, using principal component analysis (PCA). The obtained results produce the model phenotype in gait analysis i.e. the difference between vehicle and cannabinoid treated animals regarding both individual parameters and PCA.

In addition to the baseline test, the motorater test was performed altogether four times over the course of behavioral study phase:

on D7, to assess the model-specific motor defects prior to dosing, on D8, after finishing the 4-h evF, on D8, after finishing the 8-h evF, and on D9, after finishing the 24-h evF.

The kinematic assay was not performed to the animals before a minimum of 30 min after evF test.

Body Weight Monitoring. The body weight of the animals was recorded at baseline evF testing, on the day of surgery (DO), and daily thereafter.

Endpoint, Blood Samples and Tissue Processing. On D9, after the last motorater test, the behavioural study phase were completed by choosing 6 rats per group to continue into the PK-phase. The rest of animals were euthanized by an overdose of $CO_2$, and decapitation.

Upon the endpoint day of the PK.-phase, on D11, the rats were terminally anesthetized with pentobarbital (60 mg/kg Mebunat). Blood samples were collected via cardiac punctures, and plasma isolated by centrifugation with 2000×g for 10 min. Separated plasma samples were transferred into clean tubes and stored in −80° C. until shipment.

Next, the animals were transcardially perfused first with PBS. Brains were detached from the skull and snap-frozen in liquid $N_2$. Thereafter, the brain samples were stored in −80° C. until shipment.

Lumbar DRGs were prepared to sight, and harvested from both sides. Lumbar DRGs L4-L6 from each side were pooled in a pre-labelled 2-ml tube (ipsilateral DRGs into one tube; contralateral DRGs to another), and post-fixation performed in 10% commercial formalin for 24 h (+4° C.). Finally, the DRG samples were briefly flushed with 0.1 M PBS, and stored in the buffer in +4° C. until and during the shipment.

Sample Storage and Shipment. Study samples are stored at Charles River Finland.

General Health Status and Humane Endpoints. Animals were monitored daily by laboratory personnel. In the case that general health status of an animal has significantly worsened, it was sacrificed by an overdose of $CO_2$, and decapitated. Definitions of acceptable endpoints include: no spontaneous movements and inability to drink or eat in a 24-h observation period, massive bleeding, spontaneous inflammation, missing anatomy, swelling or tumors larger than 20 mm, and inability to right itself for a 30-s period.

In addition, the following model specific end-point criteria apply: the wound suture opens three times (at the first time new stitching was done; at the second time, tissue glue may be used in addition); wound inflammation that worsens despite of 48 h treatment; paralysis of any extent of either hindleg; and automutilation which sometimes is associated with neuropathic pain models.

Statistical Analysis. All values are presented as group mean±standard error of the mean. All statistical analyses were conducted with a significance level of α=0.05, using GraphPad Prism statistical program (Version 8, GraphPad Software, Inc., San Diego, CA).

Levels of significance are reported, based on GraphPad definitions, as follows:

**** $p < 0.0001$, extremely/highly significant

*** $p < 0.001$, extremely/highly significant

** $p < 0.01$, very significant

* $p < 0.05$, significant $p < 0.1$, an established trend towards significance

An additional symbol (•) has been included in the significance scale, with the notion of ($p < 0.1$), referring to 90-95% chance of the indicated effect being genuine and true effect—and, correspondingly, 5-10% chance of the effect being false. The statistical software utilized refers to this significance level as "established trend towards significance".

Nevertheless, as these comparisons are considered as "planned comparisons", and there is 'found variance' combined with the small group size, a more conservative method with adjusting the p-values is recommended to be used. Therefore, Dunnett's multiple comparisons test was used as the post hoc test.

Otherwise, the guidelines given in the study protocol section of "Statistical Analysis" were followed.

Results

Welfare and Premature Terminations. The overall animal welfare in the study was good. Some animals (approximately 2% of animals) were terminated due to penis prolapse or other severe issue in the area. This has been seen in earlier studies as well and is related to the SNL model. The reason for this is unknown, but it is likely that neuropathy-like symptoms may manifest as itch, numbness, etc., and that the model induction somehow evokes this symptom. There were more rats that experienced issues in grooming, but they recovered due to supportive care.

In case of animals being terminated or found dead: One animal died very suddenly upon second dosing on D10; the second one displayed defective breathing during the surgery and was then found dead soon after operation end.

No Significant Difference In Body Weight Of Treatment Groups Throughout The Study. Body weight development of the treatment groups during the study is presented in FIG. 1. Body weights (BW) were measured upon baseline testing (BL). Thereafter, the mice were weighted daily, until the endpoint samplings on D9, and for the rest of the animals, on D11.

Figure 1:
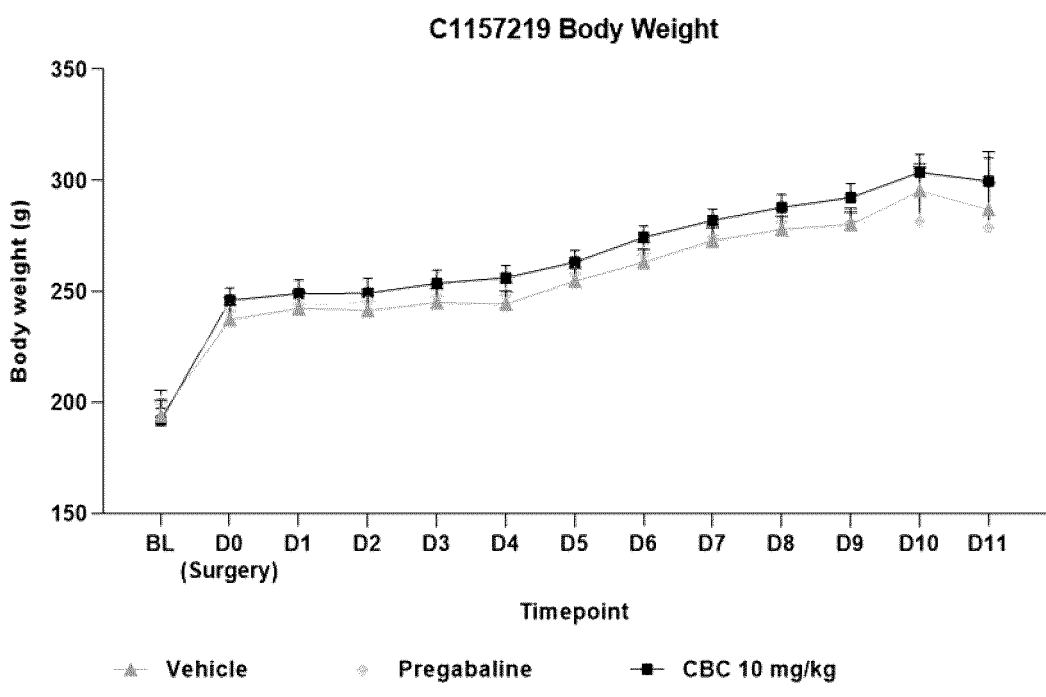
FIG. 1 depicts animal body weight changes over the time points studied in Example 3 for the different treatment groups: pregabalin, cannabichromene (CBC) at 10 mg/kg, and vehicle, showing no significant differences in weight between treatment groups.

FIG. 1 shows that the body weight effects of the three groups, vehicle, pregabalin, and CBC at 10 mg/kg were not significantly different over the course of the study. Data is presented as Mean+SEM (Group sizes: Vehicle, n=12; Pregabalin; n=12; CBC 10 mg/kg, n=9). No statistical significances were observed when comparing different treatment groups to vehicle treated animals (two-way ANOVA, Tukey's post hoc).

Cannabichromene Reduces Tactile Allodynia. In this study, mechanical hypersensitivity to touch stimuli was defined at six time points by using electronic von Frey (evF) device along with the attached analysis software (Somedic®, Sweden).

Mechanical allodynia was assessed by evF test prior to SNL surgery (baseline), to define the individual sensitivity levels of the study animals. Next, the evF was performed on D7 post-SNL, to assess the hypersensitivity evoked by SNL, and to provide pre-dosing values. On D8, the animals were subjected to evF test at 2 h, 4 h, and 8 h post-dosing (PD).

Subsequently, the test was performed at 24 h PD, i.e. on D9. In order to simplify and rationalize both figures and the text, the following terms will be used for the time points from here onwards:

| Baseline | → BL |
|---|---|
| D7 | → Pre-Dosing |
| D8 2 h PD | → 2 h PD |
| D8 2 h PD | → 2 h PD |
| D8 4 h PD | → 4 h PD |
| D8 8 h PD | → 8 h PD |
| D9 | → 24 h PD |

In the following sections (7.3.1-7.3.4), the results of evF-measurements are presented as mean percentage from baseline. This value represents normalized results, where the varying baseline values of individual animals have been taken into account. An increase of the value thus points to reversed hypersensitivity, while a lower column points to more severe hypersensitivity. Mean baseline (100%)—and mean pre-dosing level are indicated in the figures.

The assessment of compound effects and comparisons between treatments have been performed to reveal differences: within time point, between groups (groups compared at each distinct time point); and within group, between time points (baseline, pre-dosing, 2 h PD, 4 h PD, 8 h PD and 24 h PD).

In addition, the results are shown as curves, to assess the total effect of each dose mixture during the 24 h PD period, by analyzing the total area under the curve.

Furthermore, to focus on possibly prolonged treatment effects and the persisting effect differences, separate analysis was performed merely from the results obtained in the final time point, i.e. 24 h PD.

Model Induction Efficacy and Result Values. Mechanical allodynia was assessed by evF test prior to SNL surgery (baseline), to define the individual sensitivity levels of the study animals. Subsequently the evF was performed on D7 post-SNL, to assess the hypersensitivity evoked by the SNL surgery, and to provide pre-dosing sensitivity values for the following treatment comparisons. The difference between baseline and D7 (=pre-dosing) illustrates the intensity of the model, providing a window from the treatments to affect.

Figure 2:
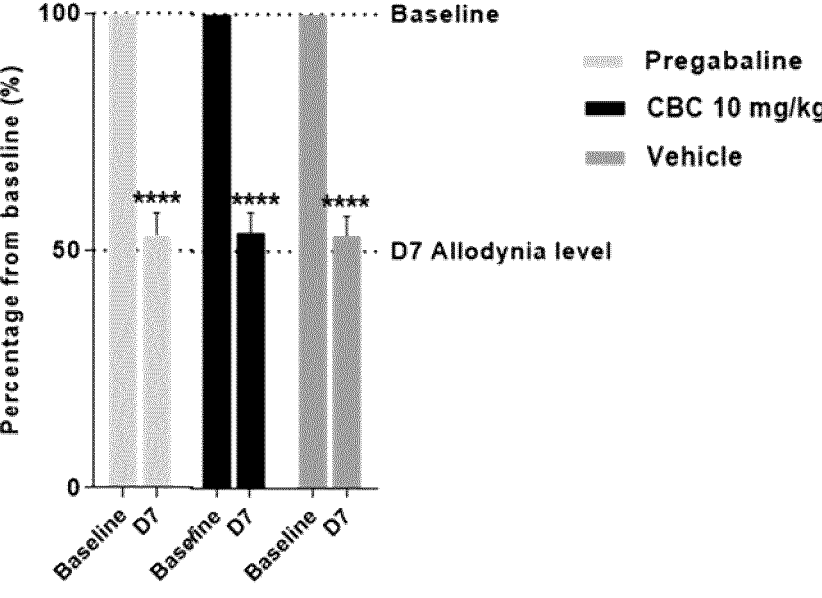
FIG. 2 provides validation of the Spinal Nerve Ligation (SNL) model. The data confirms the presence of Allodynia 7 days after SNL surgery in all groups prior to the onset of treatment effects of cannabichromene on the intensity of spinal nerve ligation (SNL) induced mechanical hypersensitivity measured by the evF. Data is presented as percentage from baseline+SEM for pregabalin, CBC 10 mg/kg, and vehicle.

FIG. 2 shows validation of Spinal Nerve Ligation model. The data presented confirm the presence of Allodynia 7 days after SNL surgery in all groups prior to the onset of treatment. The chare presents the effects of cannabichromene on the intensity of SNL-induced mechanical hypersensitivity measured by the evF. Data is presented as percentage from baseline+SEM for each group. (Group sizes: Vehicle, n=12; pregabalin, n=12; CBC 10 mg/kg, n=9). Statistical significances: **** $p < 0.0001$, vs. Baseline (two-way ANOVA, Sidak's post hoc).

SNL surgery produced robust and reproducible tactile allodynia in all groups, showing highly significant differences between baseline and D7 ($p < 0.0001$, two-way ANOVA, Sidak's post hoc) (FIG. 2), as shown by adjusted p-values in Table 2. Thus, it was confirmed that the animals were operating at a significant functional deficit after SNL surgeries.

Table 2 shows adjusted p-values (Baseline vs. D7) for FIG. 2. D7 refers to the time point which may be referenced interchangeably as "pre-dosing".

TABLE 2

| Adjusted p-values (Baseline vs. D7) for FIG. 2. | | | | |
|---|---|---|---|---|
| Post-SNL vs. BL | Predicted (LS) mean diff. | Significant? | Summary | Adjusted P Value |
| Vehicle | 46.6 | Yes | **** | <0.0001 |
| Pregabalin | 46.58 | Yes | **** | <0.0001 |
| CBC 10 mg/kg | 45.98 | Yes | **** | <0.0001 |

In order to consider the individual sensitivity levels of the study animals, and secure fair comparisons between different animals, the results were normalized to the baseline, to produce [percentage from baseline]—values. These values were obtained by proportionating each individual raw PWT result to each individual baseline value. The values were then averaged into group means and analyzed accordingly. The group comparisons for each panel are reported herein in tables associated with relevant figures.

Cannabichromene Exhibits A Prolonged Anti-Nociceptive Effect Indicated by Reduction of mechanical Allodynia and Reversal of Mechanical Hypersensitivity. To evaluate the effect of administration of cannabichromene on SNL-induced mechanical hypersensitivity, pregabalin (positive control; 50 mg/kg), CBC (10 mg/kg) and vehicle groups were compared.

Figure 3:
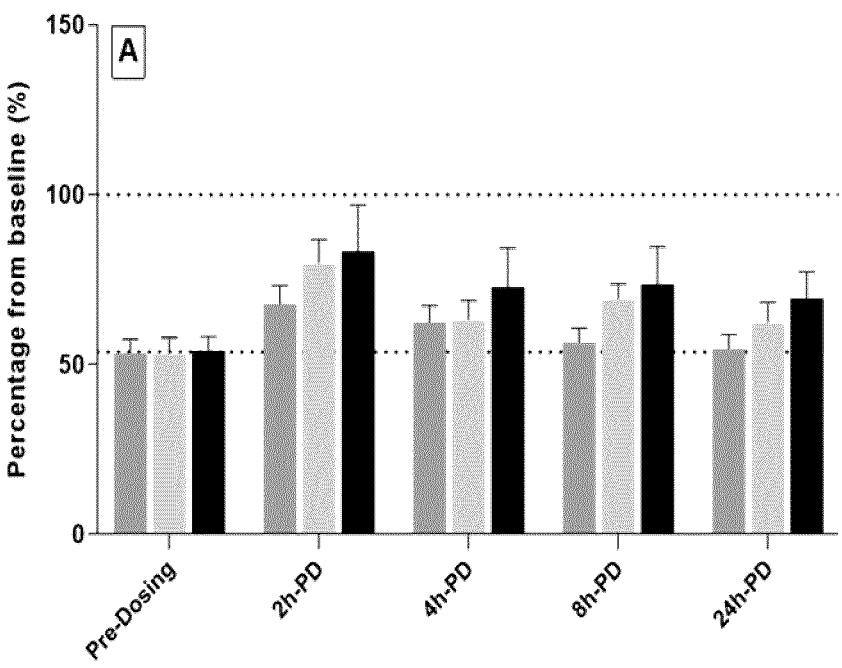
FIG. 3 depicts the effects of multiple distinct doses on the intensity of SNL-induced mechanical hypersensitivity measured by the evF. Data is presented as percentage from baseline+SEM for each group: Vehicle, Pregabalin, and CBC 10 mg/kg, between treatment groups (Panel A), and within a treatment group at different time periods (Panel B).
Figure 3:
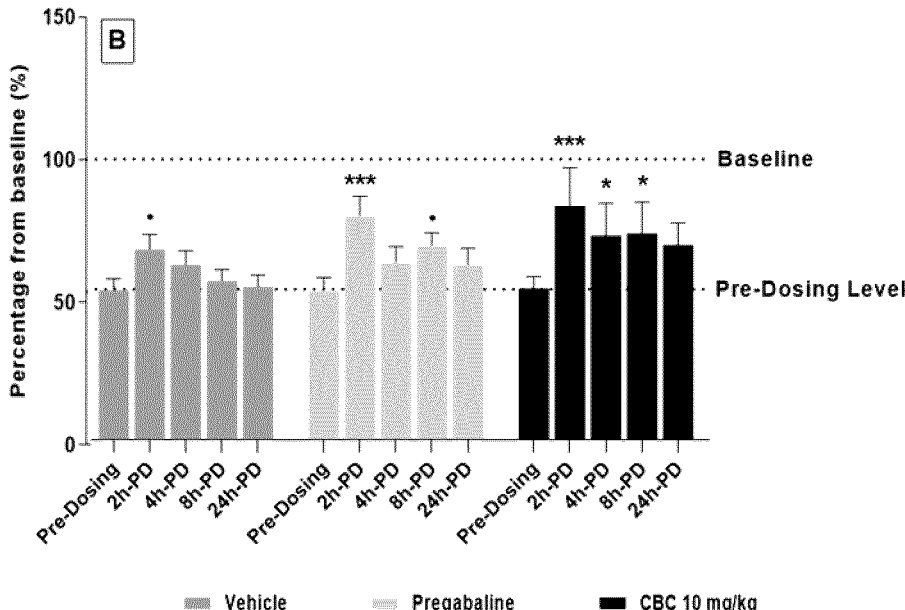

FIG. 3 illustrates the performed comparisons. The effects of multiple distinct doses of CBC on the intensity of SNL-induced mechanical hypersensitivity measured by the evF. Data is presented as percentage from baseline+SEM for each group. (Group sizes: Vehicle, n=12; Pregabalin, n=12; CBC 10 mg/kg, n=9).

Statistical Significances:

A) * $p < 0.05$,  $p < 0.01$, * $p < 0.001$, **** $p < 0.0001$, vs. Vehicle

B) * $p < 0.05$,  $p < 0.01$, * $p < 0.001$, **** $p < 0.0001$, vs. D7 (two-way ANOVA, Dunnett's post hoc).

CBC 10 mg/kg appears to evoke a trend of reversing hypersensitivity. Nonetheless, according to the conducted two-way ANOVA between-group comparisons, there were no significant treatment effect or treatment-time interaction effect present in this subset of groups (p>0.05, two-way ANOVA).

Table 3A provides adjusted p-values for FIG. 3 Panel A. The 2 groups compared to vehicle at each time point.

TABLE 3A

| Adjusted p-values for FIG. 3 Panel A | | | |
|---|---|---|---|
| | Predicted (LS) mean diff. | Summary | Adjusted P Value |
| Pre-Dosing | | | |
| Vehicle vs. Pregabalin | −0.02247 | ns | >0.9999 |
| Vehicle vs. CBC 10 mg/kg | −0.627 | ns | 0.9969 |
| 2 h-PD | | | |
| Vehicle vs. Pregabalin | −12.08 | ns | 0.298 |
| Vehicle vs. CBC 10 mg/kg | −15.45 | ns | 0.1911 |
| 4 h-PD | | | |
| Vehicle vs. Pregabalin | −0.8299 | ns | 0.9937 |
| Vehicle vs. CBC 10 mg/kg | −10.25 | ns | 0.4624 |
| 8 h-PD | | | |
| Vehicle vs. Pregabalin | −12.91 | ns | 0.2542 |
| Vehicle vs. CBC 10 mg/kg | −17.12 | ns | 0.1357 |
| 24 h-PD | | | |
| Vehicle vs. Pregabalin | −7.967 | ns | 0.5753 |
| Vehicle vs. CBC 10 mg/kg | −14.84 | ns | 0.2151 |

Table 3B provides adjusted p-values for FIG. 3, Panel B. Time points within each group compared to pre-dosing value of the same group.

TABLE 3B

| Adjusted p-values for FIG. 3, Panel B | | |
|---|---|---|
| | Predicted (LS) mean diff. | Summary | Adjusted P Value |
| Pregabalin | | | |
| Pre-Dosing vs. 2 h-PD | −26.59 | *** | 0.0003 |
| Pre-Dosing vs. 4 h-PD | −9.891 | ns | 0.3622 |
| Pre-Dosing vs. 8 h-PD | −16.03 | ns | 0.0521 |
| Pre-Dosing vs. 24 h-PD | −9.176 | ns | 0.4291 |
| CBC 10 mg/kg | | | |
| Pre-Dosing vs. 2 h-PD | −29.36 | *** | 0.0006 |
| Pre-Dosing vs. 4 h-PD | −18.71 | * | 0.0487 |
| Pre-Dosing vs. 8 h-PD | −19.64 | * | 0.0355 |
| Pre-Dosing vs. 24 h-PD | −15.44 | ns | 0.1334 |
| Vehicle | | | |
| Pre-Dosing vs. 2 h-PD | −14.54 | ns | 0.09 |
| Pre-Dosing vs. 4 h-PD | −9.084 | ns | 0.4382 |
| Pre-Dosing vs. 8 h-PD | −3.141 | ns | 0.969 |
| Pre-Dosing vs. 24 h-PD | −1.232 | ns | 0.999 |

Interestingly, within group comparisons (FIG. 3, Panel A; Table 3A) displayed a highly significant time-bound effect by CBC 10 mg/kg treatment, showing dynamic response to administration peaking at 2 hours Post-Dosing (2 h-PD; $p=0.0006$) and gradually reverting back to baseline thereafter. Furthermore, a statistical significance was found at 4 h PD ($p=0.0487$), and even at 8 h PD ($p=0.0355$). These results confirm the prolonged anti-nociceptive effect of Cannabichromene up to 8 hours post administration (FIG. 3, Panel B; Table 3B).

It is worth noting that at 24 h post-dosing, the result value still was above the Pre-dosing level (PD); however, the difference from Pre-dosing level at 24 h PD, remains non-significant for CBC-treated group ($p=0.1334$, two-way ANOVA, Dunnett's post hoc) (FIG. 3).

Cannabichromene Shows Superior Analgesic Effects Compared to Reference Article (Pregabalin). A Single treatment with CBC 10 mg/kg appeared to induce a strong analgesic effect indicated by a highly significant reduction in hypersensitivity due to pain.

Figure 4:
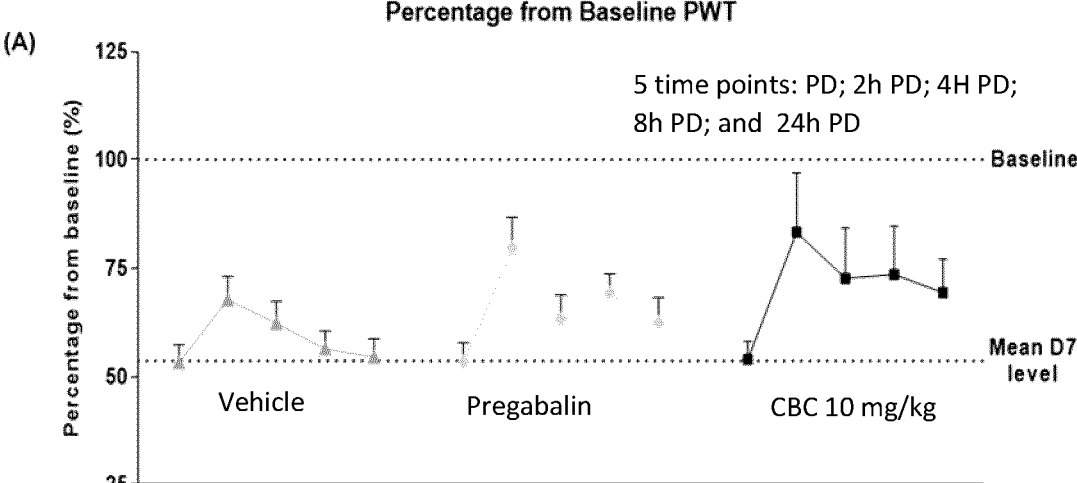
FIG. 4 provides a measurement of analgesic effect based on Area Under the Curve (AUC) and percent Paw Withdrawal Threshold (PWT). Panel A shows percent change from baseline PWT and Panel B shows AUC for the corresponding % PWT curves for vehicle, pregabalin and CBC 10 mg/kg treatment groups.
Figure 4:
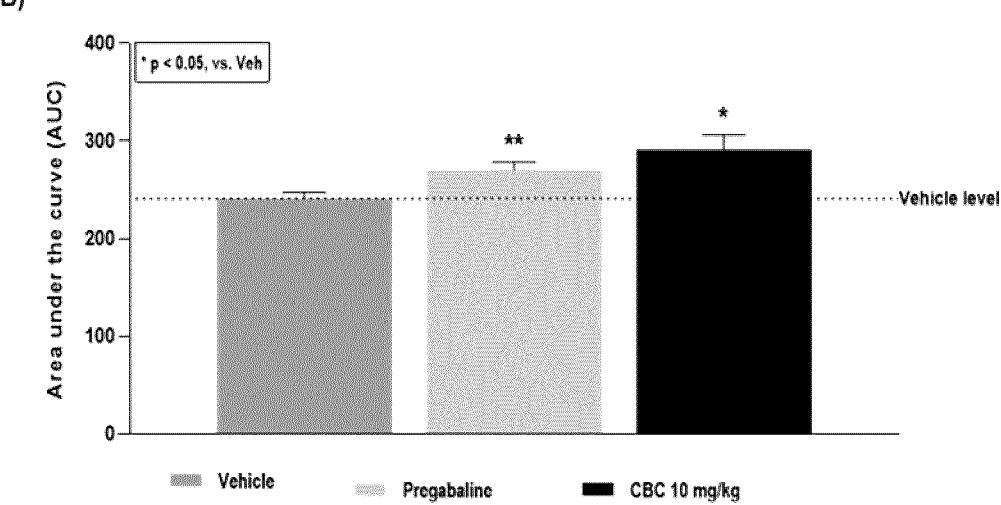

FIG. 4 provides data regarding Area Under the Curve (AUC) for the group subset with control groups (vehicle, pregabalin and CBC 10 mg/kg). Data is presented as percentage from baseline PWT+SEM for each group (Panel A), and as AUC for the corresponding curves (Panel B). Panel A: Area Under the Curve (AUC) was measured to evaluate % Paw Withdrawal Threshold pre-dosing, and at 2 h PD, 4 h PD, 8 h PD and 24 h PD. Panel B: The anti-nociceptive effect of Cannabichromene compared to Vehicle ($p=0.0024$) was found to be superior to Pregabalin compared to Vehicle ($p=0.0536$). Group sizes: Vehicle, n=12; Pregabalin, n=12; CBC 10 mg/kg, n=9). AUC: Are Under the Curve. PWT: Paw Withdrawal Threshold. Statistical significances: * p<0.05, ** p<0.01, vs. Vehicle (Welch's unpaired t-test).

Table 4 shows the adjusted p-values for AUCs presented in FIG. 4. Pregabalin (serving as the reference article for reversing tactile allodynia) and CBC 10 mg/kg compared to the vehicle AUC.

TABLE 4

| Adjusted p-values for AUCs presented in FIG. 4 | | | |
|---|---|---|---|
| Dunnett's multiple comparisons test | Mean Diff. | Summary | Adjusted P Value |
| Vehicle vs. Pregabalin | −29.80 | • | 0.0536 |
| Vehicle vs. CBC 10 mg/kg | −50.00 | ** | 0.0024 |

As shown in FIG. 4, Area Under the Curve (AUC) was measured to evaluate % Paw Withdrawal Threshold pre-dosing, and at 2 h PD, 4 h PD, 8 h PD and 24 h PD (FIG. 4, Panel A). The anti-nociceptive effect of cannabichromene compared to Vehicle ($p=0.0024$) was found to be superior to pregabalin compared to vehicle ($p=0.0536$) (FIG. 4, Panel B; Table 4). Long-term monitoring of animals up to 48 hours may further elucidate the value of AUCs.

These results of this Example confirm that cannabichromene potently acts to decrease pain-induced hyperalgesia and tactile allodynia, and need not be utilized together with any other cannabinoid to achieve this effect.

Remarkably, these data also suggests a prolonged anti-nociceptive effect of cannabichromene that last up to 8 hours after one-time administration, an effect that was not observed with pregabalin treatment.

Cannabichromene Effectively Alleviates Pain Demonstrated by Improvement in Impaired Mobility in SNL Rat Model. The fine motor capabilities and the gait of the animals were evaluated at the baseline and four times after the SNL surgery, 2, 5, 9 and 24 hours post-dosing (PD) in the MotoRater system using the kinematic movement analysis of altogether 97 separate parameters that were recorded. Principal component analysis (PCA) was performed for the parameter data to reduce the number of variables, and to reveal correlations between separate parameters.

Figure 5:
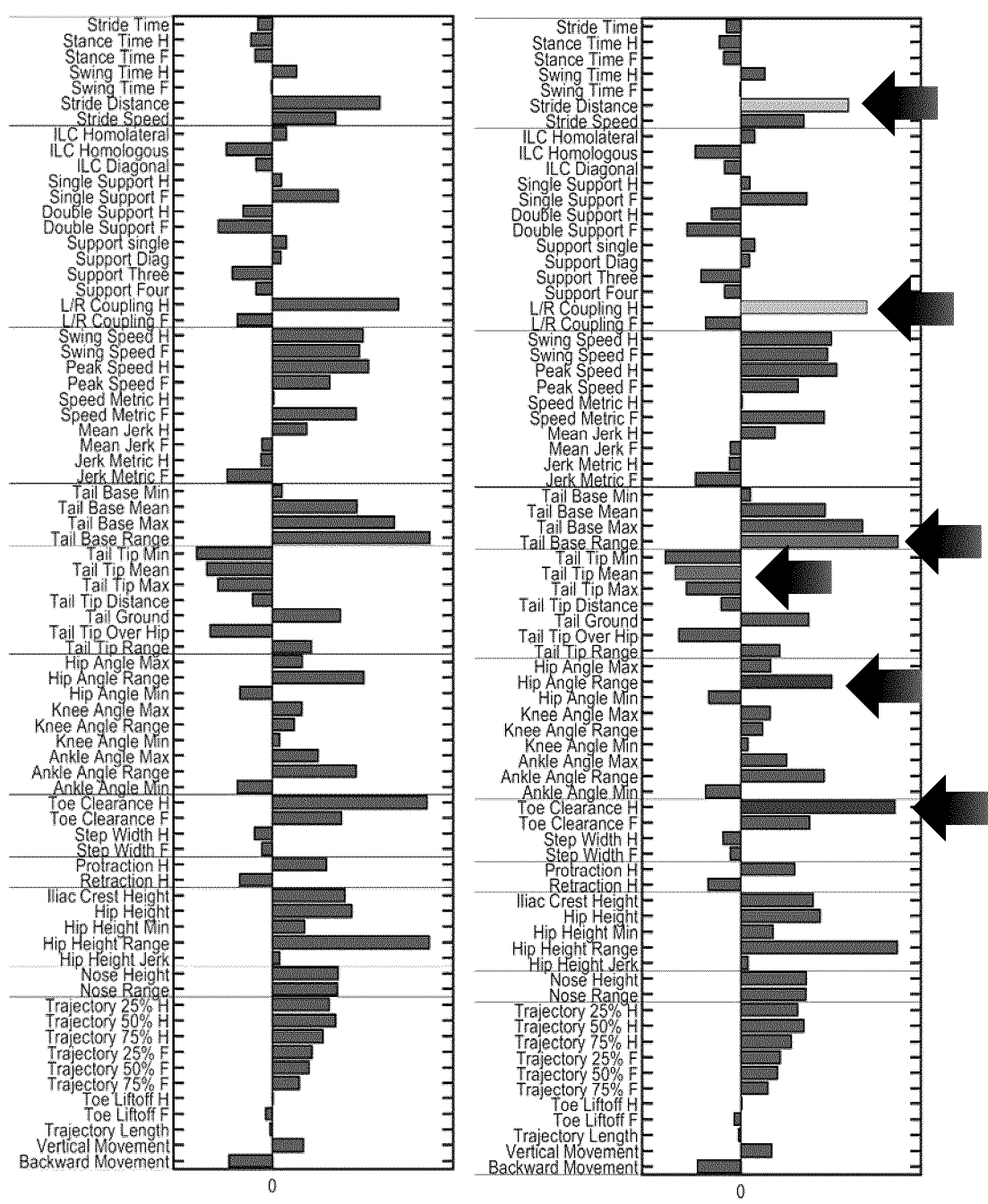
FIG. 5 depicts discriminant vector bar graph presenting SNL-induced motor phenotype, based on PCA of baseline (BL) and D7 differences in all study groups. Left panel: the original vector graph. Right panel: those characteristic gait features, that represent the SNL motor phenotype the most; highlighted and specified with arrows.

FIG. 5 provides a discriminant vector bar graph presenting SNL induced motor phenotype, based on PCA of BL and D7 differences in all study groups. Left Panel: the original vector graph. Right Panel: those characteristic gait features, that represent the SNL motor phenotype the most; highlighted and specified with arrows. (Group sizes: Vehicle, n=12; Pregabalin; CBC 10 mg/kg, n=9).

PCA combines all the parameter data, reveals correlations between them, and provides an overall view of the fine motor and gait characteristics of the SNL operated rats. SNL-induced motor phenotype, based on PCA of BL and D7 differences in all study groups, is presented in the bar graph (FIG. 5) to illustrate which parameters changed after SNL (zero=BL). The bar length and direction indicate the weight how much each parameter is contributed in the overall score. The motor phenotype of SNL model can be characterized and interpreted as the following combination of changes in the gait features (FIG. 5):

The overall speed is increased which is mainly due to longer stride distance (increased step length).

The interlimb coordination is not dramatically changed, except the asymmetry in the hind limb left-right alternation rhythm is increased (L/R Coupling H).

The overall hip height and vertical range of hip movement are increased (Tail Base mean/max/range, hip height, hip height range, iliac crest height).

Tail tip position is lower (Tail tip min/mean/max).

Hip angle range is increased.

Hind limb toe clearance is increased.

Cannabichromene Treatment Shows Promising Improvement in Overall Kinematics and Functional Ability of SNL Pain Model. Gait scores are assed as follows.

Figure 6:
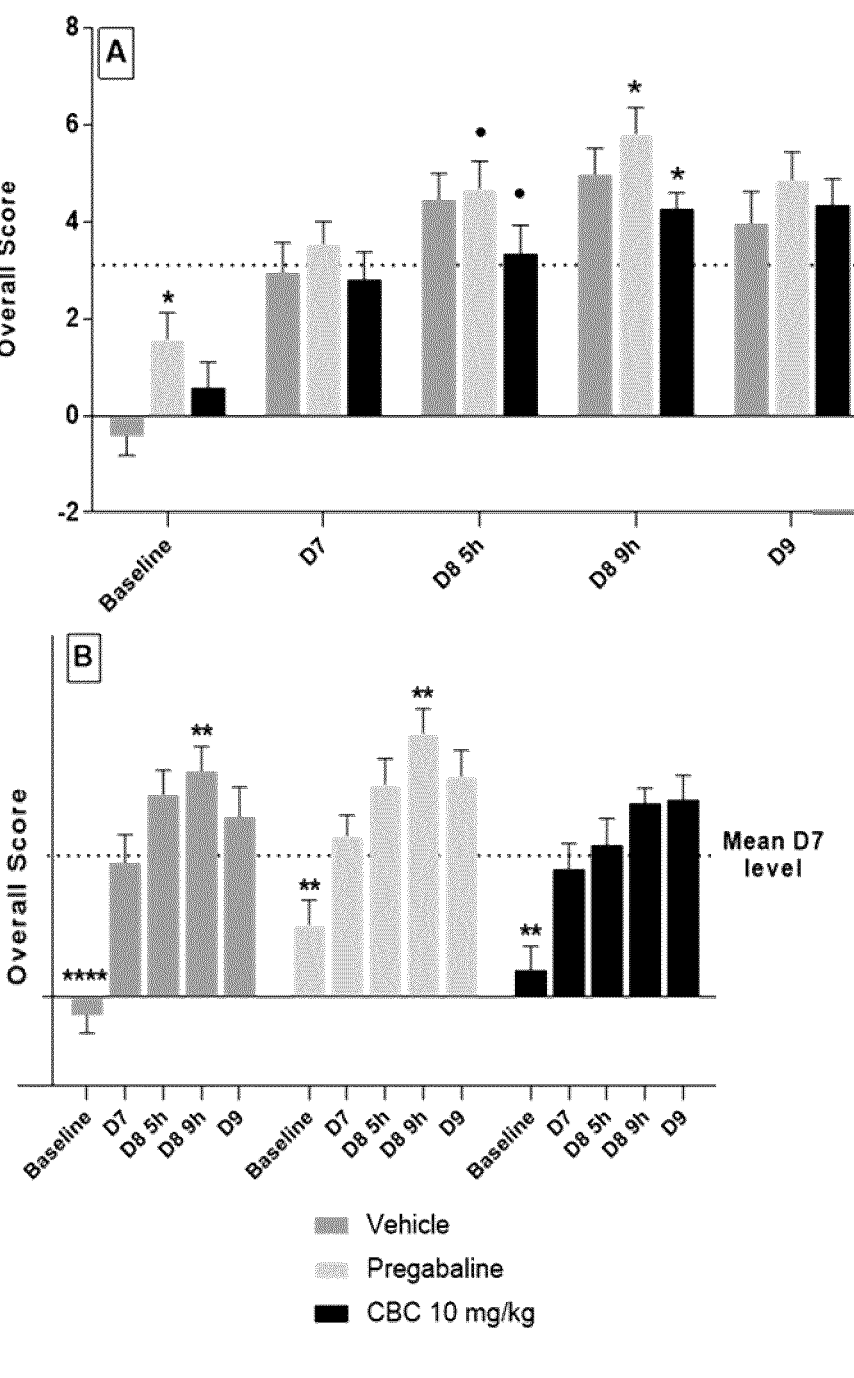
FIG. 6 shows overall gait performance (gait overall score) within the subset of Vehicle, Pregabalin, and 10 mg/kg CBC groups. Panel A compares treatment groups to each other at different time points, and Panel B compares different time points within a treatment group.

FIG. 6 illustrates overall gait performance (gait overall score) within the subset of 10 mg/kg CBC, vehicle and pregabalin groups. Data is presented as Mean z-score+SEM for each group. Group sizes: vehicle, n=12; pregabalin, n=12; CBC 10 mg/kg, n=9. A)* p<0.05, vs. vehicle; B) p<0.1; * p<0.05,  p<0.01, * p<0.001, **** p<0.0001, vs. D7 (two-way ANOVA, Dunnett's post hoc). Statistical significances: Panel A) * p<0.05, vs. Vehicle; Panel B) p<0.1; * p<0.05,  p<0.01, * p<0.001, **** p<0.0001, vs. D7 (two-way ANOVA, Dunnett's post hoc).

Figure 7:
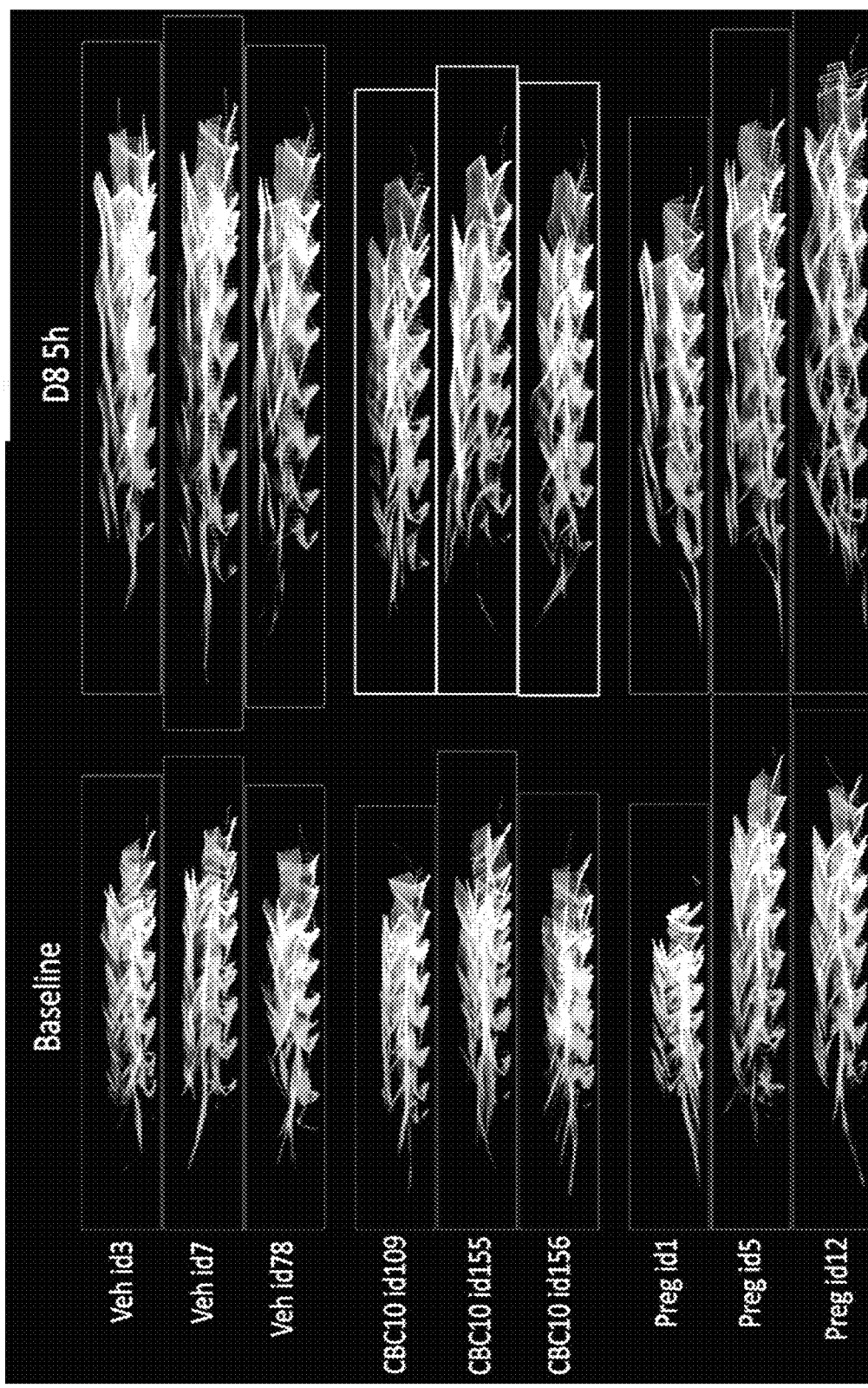
FIG. 7 is an illustration overall gait performance of SNL rats. Still image motiongraphs of SNL-animal locomotion pre- and post-treatment is shown with cannabichromene. Motiongraphs illustrate a one-second period of motions, as an example of kinematic gait performance evaluation of videos recorded from three different sides. Left side panels display baseline and right-side panels show the mobility of the same animal 5 h post-dosing.

FIG. 7 illustrates SNL rats overall gait performance. A still image of SNL-animal locomotion pre- and post-treatment with cannabichromene is provided. Motiongraphs illustrate a one-second period of motions, as an example of kinematic Gait performance evaluation of videos recorded from three different sides. The motiongraphs exhibit one-second captured from lateral view. While greyscale is currently used to illustrate animal locomotion, the motiongraphs of FIG. 7 originally employed red color to illustrate body parts from right side limbs (SNL surgery side) and blue color from left (Normal limb). The tail and nose tip were originally shown green. Left side panels display baseline and right-side panels show the mobility of the same animal 5 h post-dosing. Three different animals are shown for each vehicle, cannabichromene and pregabalin treatment. Preg: pregabalin; CBC10: cannabichromene at 10 mg/kg; Veh: vehicle group. D8 5 h: Day 8-5 hours post-dosing. Id: Animal identification.

The overall gait scores (FIG. 6 and FIG. 7) reflect all of the changes found on PCA analysis, together (using the discriminant direction vector as a "yardstick"), and are presented in a way that the average score at baseline is equal to zero.

The average score of all study groups at D7 is equal to 3.107 ('z-scores'). Clearly, a decrease of the overall score means that the gait performance has changed towards to the pre-SNL status or Baseline (BL) interpreted as improvement in impaired mobility.

Cannabichromene at 10 mg/kg did not show a significant reduction in overall Gait score compared to Vehicle (FIG. 6, Panel A). Nonetheless, cannabichromene treatment demonstrated a trend towards better overall gait score when compared to pregabalin at 5 h PD (p=0.07693) and 9 h PD (p=0.04717), as compared to pregabalin (FIG. 6, Panel A).

Within group comparisons did not identify a significant time-bound overall gait score difference in CBC treatment group (FIG. 6, Panel B).

These striking results indicate a superior effect of CBC over pregabalin, which was further investigated to diligently examine the specific gait feature changes characterizing the typical motor performance (FIG. 7-FIG. 14).

Table 5 provides overall kinematic gait scores: between-group comparisons at each time point. All groups compared to Vehicle at each time point: Adjusted p-values are presented for FIG. 6, Panel A.

Table 6 provides overall kinematic gait scores: within-group comparisons at each time point versus Day 7 Baseline (Prior to Treatment). Adjusted p-values are presented for FIG. 6, Panel B. Statistical Significance: p<0.1; * p<0.05,  p<0.01, * p<0.001, **** p<0.0001.

TABLE 5

Overall Kinematic Gait Scores: Between-Group Comparisons at each Time point For FIG. 6 Panel A

| | Predicted (LS) mean diff. | Summary | Adjusted P Value |
|---|---|---|---|
| Baseline | | | |
| Vehicle vs. Pregabalin | −2.013 | * | 0.0122 |
| Vehicle vs. CBC 10 mg/kg | −1 | ns | 0.3441 |
| D7 | | | |
| Vehicle vs. Pregabalin | −0.5896 | ns | 0.6356 |
| Vehicle vs. CBC 10 mg/kg | 0.1511 | ns | 0.9738 |
| D8 5 h | | | |
| Vehicle vs. Pregabalin | −0.2262 | ns | 0.9333 |
| Vehicle vs. CBC 10 mg/kg | 1.116 | ns | 0.2709 |
| D8 9 h | | | |
| Vehicle vs. Pregabalin | −0.8408 | ns | 0.4124 |
| Vehicle vs. CBC 10 mg/kg | 0.654 | ns | 0.6388 |
| D9 | | | |
| Vehicle vs. Pregabalin | −0.8531 | ns | 0.418 |
| Vehicle vs. CBC 10 mg/kg | −0.4602 | ns | 0.8117 |

TABLE 6

Overall Kinematic Gait Scores: Within Group Comparisons For FIG. 6 Panel B

| | Predicted (LS) mean diff. | Summary | Adjusted P Value |
|---|---|---|---|
| Pregabalin | | | |
| D7 vs. Baseline | 1.964 | ** | 0.0067 |
| D7 vs. D8 5 h | −1.135 | ns | 0.204 |
| D7 vs. D8 9 h | −2.27 | ** | 0.0013 |
| D7 vs. D9 | −1.271 | ns | 0.1451 |
| CBC 10 mg/kg | | | |
| D7 vs. Baseline | 2.236 | ** | 0.0078 |
| D7 vs. D8 5 h | −0.5337 | ns | 0.8713 |
| D7 vs. D8 9 h | −1.516 | ns | 0.1329 |
| D7 vs. D9 | −1.619 | ns | 0.1193 |
| Vehicle | | | |
| D7 vs. Baseline | 3.388 | **** | <0.0001 |
| D7 vs. D8 5 h | −1.498 | • | 0.0554 |
| D7 vs. D8 9 h | −2.019 | ** | 0.0051 |
| D7 vs. D9 | −1.008 | ns | 0.2964 |

Cannabichromene Strongly Improves Pain-Induced Functional Hip Impairment and Increases Limb Mobility. "MotionGraphs" were created of three animals from each group (9 animals in total) illustrating gait performance at baseline and on D8 5 h post dose.

FIG. 7 demonstrates three motiongraphs for each treatment group illustrating one-second period of motion. The same individual is shown at both time points on each "row" of the figure (FIG. 7). These 3×3=9 example animals were selected such that they are close to their group mean in overall Gait score at D8 5 h PD time point. Visualization of videos and evaluation of parameters were carefully conducted for 97 different parameters. Each parameter was further analyzed to characterize discriminant factors affected by pregabalin or cannabichromene treatment. For example, a longer motiongraph indicates that the animal moved faster and walked longer distance during that one-second period. Gait Variables are illustrated in FIGS. 8-14. Highlighted panels demonstrate moderate or highly significant improvement (p≤0.01) in Gait parameters at different time point post-Dosing.

Table 7 represents further statistical analyses conducted to examine the effect of Treatments versus vehicle for particular Gait parameters. Kinematic gait analysis is shown, with comparison of discriminant parameters in rats received CBC or pregabalin treatment with vehicle group. Table 7 represents statistical analyses conducted to examine the effect of CBC or pregabalin treatments versus vehicle on particular Gait parameters. Statistically significant values are summarized; Adjusted p-values are presented and p≤0.01 was considered statistical significance for listed comparisons. Statistical significance was considered adjusted p-values: *p~0.01;  p≤0.01, * p≤0.001. n: number of animals in each group (df: degree of freedom).

demonstrated these benefits by showing by lower maximum hip angle (p=0.0005) and knee angle (p=0.001) with slight reduction of ankle angle (p=0.01) (also, see FIG. 14; Table 7).

Figure 8:
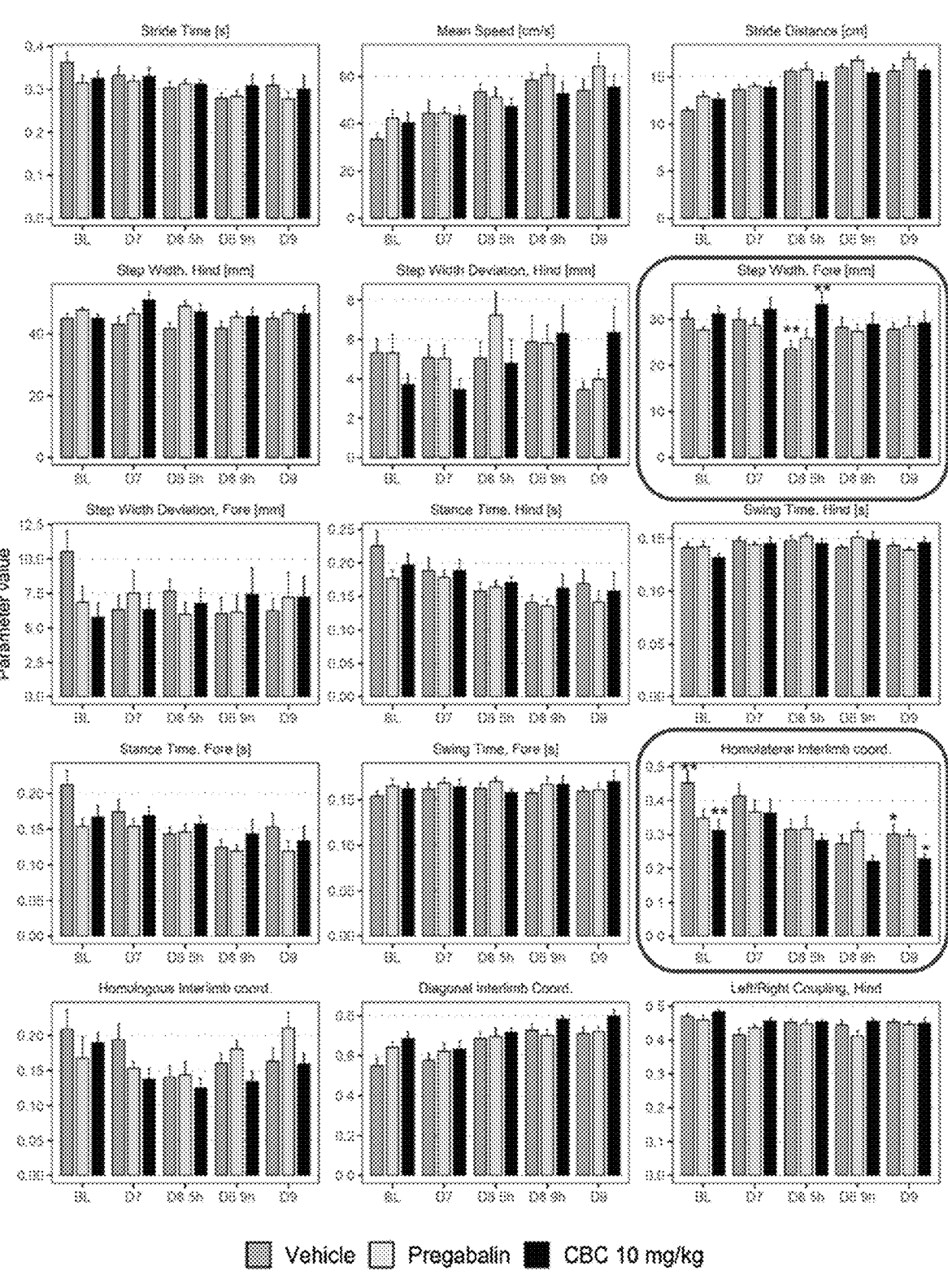
FIG. 8 illustrates limb metric gait variables at baseline, D7, D8-5 h, D8-9 h and D9 post-dosing. Highlighted panels represent statistically significant parameters observed upon treatment with cannabichromene for: Step Width—Forelimb [mm]; and Homolateral Interlimb coordination.

FIG. 8 illustrates limb metric gait variables at baseline, D7, D8-5 h, D8-9 h and D9 Post-Dosing. Highlighted panels represent statistically significant parameters observed upon treatment with cannabichromene. Statistical significances: p≤0.01 was considered significant based on adjusted p-values. Highlighted Panels: Step Width, Forelimb [mm]—D8-5 h PD: CBC vs. Vehicle: p=0.012; Homolateral Interlimb coordination Baseline: CBC vs. Vehicle: p=0.01; Homolateral Interlimb coordination—D9: CBC vs. Vehicle: *p=0.03; (Group sizes: Vehicle, n=12; Pregabalin, n=12; CBC 10 mg/kg, n=9).

TABLE 7

Kinematic Gait Analysis: Comparison of Discriminant Parameters in
Rats Receiving CBC or Pregabalin Treatment with Vehicle Group

| Timepoint | Parameter | Group2 | n2 | Stats | df | p-value | Adjusted p-value | Adjusted p-value Sig? *p ≤ 0.01 |
|---|---|---|---|---|---|---|---|---|
| D 8 5 h | Retraction, Hind [m] | CBC 10 mg/kg | 9 | 4.26 | 18.1 | 0.00047 | 0.00047 | *** |
| D 8 5 h | Hip Angle, Max [degree] | CBC 10 mg/kg | 9 | 4.29 | 16.9 | 0.000501 | 0.000501 | *** |
| D 8 5 h | Protraction, Hind [m] | CBC 10 mg/kg | 9 | −4.42 | 12.6 | 0.000746 | 0.000746 | *** |
| BL | Mean Hip Jerk [m/s3] | Pregabalin | 12 | −3.75 | 18.5 | 0.001 | 0.001 | *** |
| D 8 5 h | Knee Angle, Min [degree] | CBC 10 mg/kg | 9 | 3.78 | 17.6 | 0.001 | 0.001 | *** |
| D 8 5 h | Ankle Angle, Max [degree] | Pregabalin | 12 | −3.74 | 18.6 | 0.001 | 0.001 | *** |
| D 8 5 h | Toe Clearance, Hind [m] | CBC 10 mg/kg | 9 | 3.54 | 19 | 0.002 | 0.002 | ** |
| BL | Swing Speed Metric, Hind | CBC 10 mg/kg | 9 | −3.67 | 17.8 | 0.002 | 0.002 | ** |
| D 7 | Relative Trajectory Length, Fore | Pregabalin | 12 | −3.26 | 21.6 | 0.004 | 0.004 | ** |
| BL | Duty Cycle, Fore [%] | Pregabalin | 12 | 3.26 | 22 | 0.004 | 0.004 | ** |
| BL | Knee ROM Deviation [degree] | Pregabalin | 12 | 3.23 | 16.5 | 0.005 | 0.005 | ** |
| D 9 | Toe Clearance, Fore [m] | CBC 10 mg/kg | 7 | −3.08 | 16.2 | 0.007 | 0.007 | ** |
| D 7 | Paw Trajectory Shape 25%, Hind [%] | Pregabalin | 12 | −3.01 | 20.2 | 0.007 | 0.007 | ** |
| BL | Ankle ROM Deviation [degree] | CBC 10 mg/kg | 9 | 2.98 | 17.6 | 0.008 | 0.008 | ** |
| D 8 9 h | Hip ROM [degree] | Pregabalin | 12 | 2.85 | 21.7 | 0.009 | 0.009 | ** |
| D 8 5 h | Ankle Angle, Min [degree] | Pregabalin | 12 | −2.99 | 16 | 0.009 | 0.009 | ** |
| BL | Homolateral Interlimb coordination | CBC 10 mg/kg | 9 | 2.84 | 18.9 | 0.01 | 0.01 | ** |
| BL | Knee ROM Deviation [degree] | CBC 10 mg/kg | 9 | 2.88 | 19 | 0.01 | 0.01 | ** |
| D 8 5 h | Mean Hip Jerk [m/s3] | CBC 10 mg/kg | 9 | −3.04 | 13 | 0.01 | 0.01 | ** |
| D 8 5 h | Ankle Angle, Max [degree] | CBC 10 mg/kg | 9 | −2.85 | 17.2 | 0.011 | 0.011 | * |
| D 8 5 h | Step Width, Fore [mm] | CBC 10 mg/kg | 9 | −2.86 | 14.3 | 0.012 | 0.012 | * |
| BL | Duty Cycle [%] | Pregabalin | 12 | 2.77 | 20.8 | 0.012 | 0.012 | * |

Group 1 = vehicle versus Group 2 = as shown
n1 = 12 versus n2 = as shown

Figure 9:
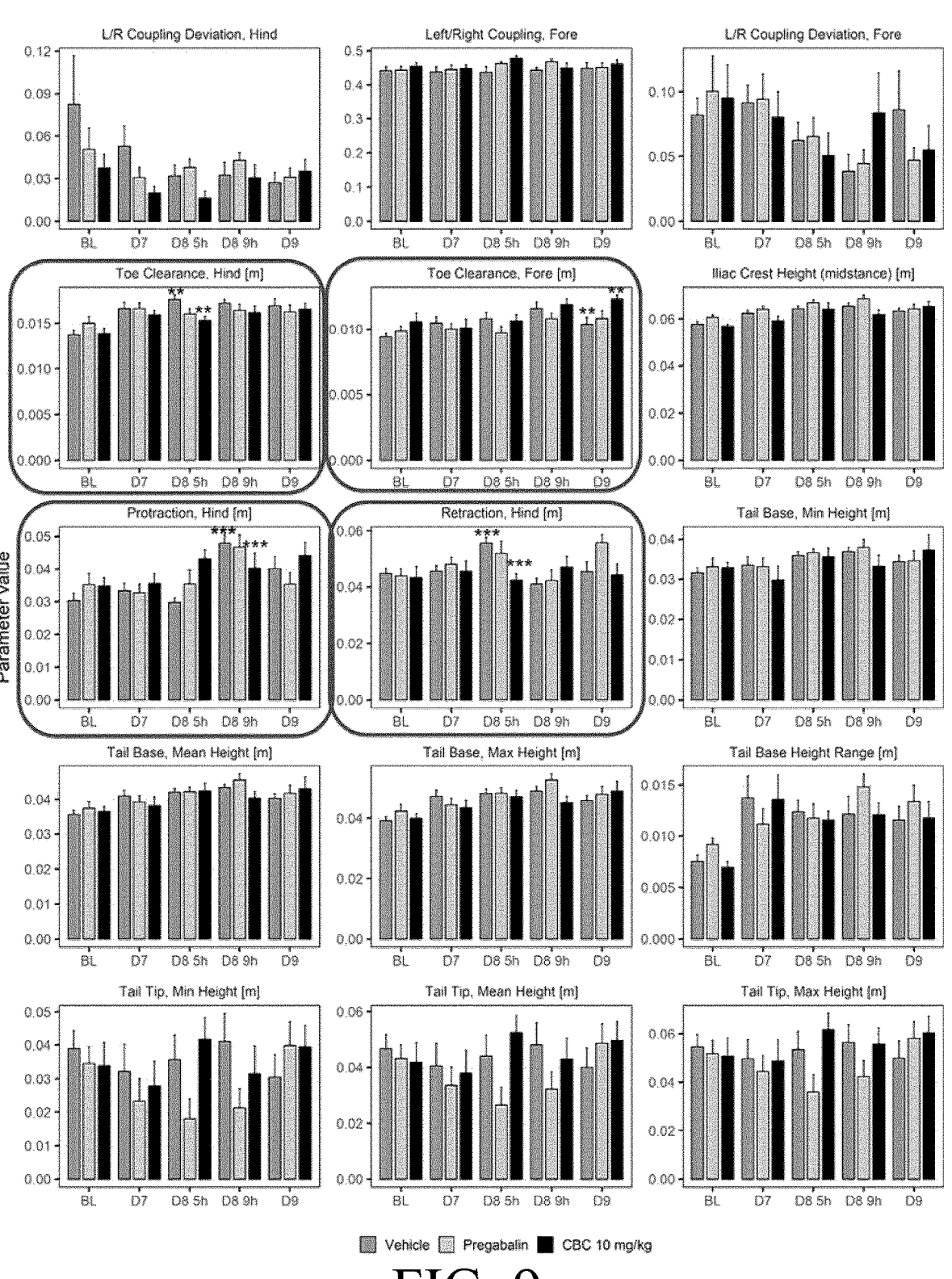

These results revealed the efficacy of cannabichromene in alleviating SNL-induced pain indicated by marked improvement in impaired hip motion (p=0.01) and significant restoration of body posture demonstrated by hind limb protraction and retraction (p=0.00047 and p=0.000746, respectively), and toe clearance (p=0.002) on Day 8-5 h PD, (FIG. 9; Table 7).

It was also observed that CBC significantly enhanced Range of Motion (ROM) on Day 8-5 h. CBC post-dosing FIG. 9 shows left/right coupling, toe and tail gait variables at baseline, D7, D8-5 h, D8-9 h and D9 Post-Dosing. Highlighted panels represent statistically significant parameters observed upon treatment with cannabichromene. Statistical significances: p≤0.01 was considered significant based on adjusted p-values. Highlighted Panels: Toe Clearance: Hindlimb [m] D8-5 h PD: CBC vs. Vehicle: p=0.002; Toe Clearance, Forelimb [m]—D9: CBC vs. Vehicle: p=0.007; Protraction, Hind limb [m]-D8-5 h PD:

CBC vs. Vehicle: *p=0.000746; Retraction, Hind limb D8-5 h PD [m]: CBC vs. Vehicle: *p=0.00047. (Group sizes: Vehicle, n=12; Pregabalin, n=12; CBC 10 mg/kg, n=9).

One striking finding was effective augmentation of inter-limb coordination shown by greater forelimb step width on Day 8-5 h PD and forelimb toe clearance on Day 9 PD (24 hours after CBC treatment) (p=0.012 and p=0.007, respectively) (FIG. 8 and FIG. 9; Table 7). These findings may be mainly a result of more efficient retraction and protraction of hind limb (p=0.00047 and p=0.000746, respectively) observed on Day 8-5 h after administration of cannabichromene.

Additional statistical analyses were conducted to further investigate the effect of Cannabichromene on discriminant Gait parameters compared to vehicle group (FIG. 15 and Table 8). These findings further confirmed the effect of CBC on enhancing SNL-induced posture and functional impairment of hindlimb indicated by enhanced hindlimb retraction, protraction, and toe clearance on Day 8-5 hours post treatment (p=0.00047, p=0.0007, p=0.00218 respectively; FIG. 15 (Panel A, Panel B, and Panel D) and Table 8.

FIG. 10 shows tail tip, swing jerk metric, hip and knee gait variables at baseline, D7, D8-5 h, D8-9 h and D9 Post-Dosing. Highlighted panels represent statistically significant parameters observed upon treatment with cannabichromene. Statistical significances: p≤0.01 was considered significant based on adjusted p-values. Highlighted Panels: Hip ROM degree—D8-9 h PD: Vehicle vs. Pregabalin: **p=0.009. (Group sizes: Vehicle, n=12; Pregabalin, n=12; CBC 10 mg/kg, n=9).

FIG. 11 shows ankle and hip height/jerk metric, tail tip metric and head rotation gait variables at baseline, D7, D8-5 h, D8-9 h and D9 Post-Dosing. Highlighted panels represent statistically significant parameters observed upon treatment with cannabichromene. Statistical significances: p≤0.01 was considered significant based on adjusted p-values. Highlighted Panels: Ankle ROM Deviation Degree Baseline: CBC vs. Vehicle: **p=0.008; Mean Hip Jerk [m/s3]—D8-5 h PD: CBC vs. Vehicle: *p=0.01; Mean Hip Jerk [m/s3] Baseline: Vehicle vs. Pregabalin: **p=0.001; (Group sizes: Vehicle, n=12; Pregabalin, n=12; CBC 10.

FIG. 12 shows toe lift, paw trajectory metric, paw distance and duty cycle gait variables at baseline, D7, D8-5 h,

TABLE 8

Kinematic Gait Analysis: Comparison of Discriminant Parameters in Rats received CBC or Pregabalin Treatment with Vehicle Group

| Timepoint | Parameter | Group2 CBC (mg/kg) | Statistic | df | p-value | Significance |
|---|---|---|---|---|---|---|
| D 8 5 h | Retraction. Hind | 10 | 4.26 | 18.1 | 0.00047 | *** |
| D 8 5 h | Hip Angle. Max | 10 | 4.29 | 16.9 | 0.000501 | *** |
| D 8 5 h | Protraction. Hind | 10 | −4.42 | 12.6 | 0.000746 | *** |
| D 8 5 h | Knee Angle. Min | 10 | 3.78 | 17.6 | 0.0014 | ** |
| BL | Swing Speed | 10 | −3.67 | 17.8 | 0.00177 | ** |
| D 8 5 h | Toe Clearance. | 10 | 3.54 | 19 | 0.00218 | ** |
| D 9[a] | Toe Clearance. | 10 | −3.08 | 16.2 | 0.00716 | ** |
| BL | Ankle ROM | 10 | 2.98 | 17.6 | 0.00813 | * |
| D 8 5 h | Mean Hip Jerk | 10 | −3.04 | 13 | 0.00953 | * |
| BL | Knee ROM | 10 | 2.88 | 19 | 0.00965 | * |
| BL | Homolateral | 10 | 2.84 | 18.9 | 0.0105 | * |
| D 8 5 h | Ankle Angle. Max | 10 | −2.85 | 17.2 | 0.0111 | * |
| D 8 5 h | Step Width. Fore | 10 | −2.86 | 14.3 | 0.0124 | * |

Comparisons made with Group1 = vehicle;
Group2 = CBC 10 mg/kg;
n1 = 12;
n2 = 9 ([a]except for Toe Clearance D 9, n2 = 7)

A trend was observed towards enhanced inter-limb coordination indicated by greater step width on day 8-5 hours post-dosing with CBC treatment compared to vehicle group (p=0.0124, FIG. 15, Panel C, Table 8).

A clear improvement in forelimb toe clearance was also indicated on Day 9 post treatment with CBC (p=0.007; FIG. 15, Panel E and Table 8). This finding, along with an improved homolateral inter-limb coordination on Day 9 post-dosing (p=0.03; FIG. 8) are particularly interesting parameters suggestive of alleviated pain in SNL rats up to 24 hours after treatment with Cannabichromene (FIG. 15, Panel E).

In this study, the effectiveness of cannabichromene in alleviating pain was confirmed, as demonstrated by marked enhancement of functional impairment, improved posture and greater inter-limb coordination and mobility after one single dose. In addition, cannabichromene showed superior efficacy in improvement of tactile allodynia and greater anti-nociceptive effect compared to pregabalin (50 mg/kg).

CBC may thus be effectively used for long-term pain management.

D8-9 h and D9 Post-Dosing. Highlighted panels represent statistically significant parameters observed upon treatment with cannabichromene. Statistical significances: p≤0.01 was considered significant based on adjusted p-values. Highlighted Panels: Paw Trajectory Shape 25%, Hind limb [%] D7: Vehicle vs. Pregabalin: p=0.007; Relative Trajectory Length, Forelimb D7: Vehicle vs. Pregabalin: p=0.004; Group sizes: Vehicle, n=12; Pregabalin, n=12; CBC 10 mg/kg, n=9).

FIG. 13 shows support metric gait variables at baseline, D7, D8-5 h, D8-9 h and D9 Post-Dosing. Highlighted panels represent statistically significant parameters observed upon treatment with cannabichromene. Statistical significances: p≤0.01 was considered significant based on adjusted p-values. No statistical significance was observed in Support Metric of mice treated with cannabichromene compared to Vehicle (Group sizes: Vehicle, n=12; Pregabalin, n=12; CBC 10 mg/kg, n=9).

FIG. 14 shows hip/knee/angle angel gait variables at baseline, D7, D8-5 h, D8-9 h and D9 Post-Dosing. Highlighted panels represent statistically significant parameters observed upon treatment with cannabichromene. Statistical significances: p≤0.01 was considered significant based on adjusted p-values. Highlighted Panels: Hip Angle, Max degree—D8-5 h PD: CBC vs. Vehicle: *p=0.000501; Knee Angle, Min Degree—D8-5 h PD: CBC vs. Vehicle: p=0.001; Ankle Angle, Min degree—D8-5 h PD: Vehicle vs. Pregabalin **p=0.009; Ankle Angle, Max degree—D8-5 h PD: CBC vs. Vehicle: *p=0.011. (Group sizes: Vehicle, n=12; Pregabalin, n=12; CBC 10 mg/kg, n=9).

FIG. 15 shows protraction, retraction and toe clearance and step width gait variables at baseline, D7, D8-5 h, D8-9 h and D9 Post-Dosing in CBC Treatment vs. vehicle. Statistical significances: p<0.01 was considered significant based on adjusted p-values. Panel A: Protraction: Hindlimb—D8-5 h PD: CBC vs. Vehicle: *p=0.000746; Panel B; Retraction: Hindlimb—D8-5 h PD: CBC vs. Vehicle: *p=0.00047; Panel C: Step Width: Forelimb—D8-5 h: CBC vs. Vehicle: * p=0.0124; Panel D: Toe Clearance Hindlimb [m]—D8-5 h PD: Vehicle vs. CBC: p=0.00218; Panel E: Toe Clearance Forelimb [m]—D9 PD: Vehicle vs. CBC: p=0.00716; (Group sizes: Vehicle; CBC 10 mg/kg, n=9).

Parameter Definitions. The following list defines each of the parameters evaluated.

Spatial-Temporal:

Stride Time=Duration of a full stride.

Mean Speed=Mean ambulatory movement speed.

Stride Distance=Distance moved during a full stride.

Stance Time (hind, fore)=Duration the paw is in contact with the floor, stance phase.

Swing Time (hind, fore)=Duration the paw is in the air, swing phase.

Mean Swing Speed (hind, fore)=Mean paw movement speed during swing phase.

Peak Swing Speed (hind, fore)=Maximum paw movement speed during swing phase.

Swing Speed Metric (hind, fore)=Ratio of the Mean Swing Speed to Peak Swing speed.

Mean Swing Jerk (hind, fore)=The degree of non-smoothness, i.e., rate of acceleration change, of a paw during middle half of swing phase.

Swing Jerk Metric (hind, fore)=Ratio of the Swing Mean Jerk to Swing Peak Speed. A normalized swing trajectory smoothness parameter.

Duty cycle (hind, fore)=Percentage of stride time the limb is in contact with the floor.

Interlimb Coordination:

Homolateral Interlimb Coordination=Proportion of whole stride duration in which ipsilateral paws are simultaneously in stance or swing phase.

Homologous Interlimb Coordination=Proportion of whole stride duration ipsilateral and contralateral fore or hind paws are simultaneously in stance or swing phase. Pace.

Diagonal Interlimb Coordination=Proportion of whole stride distance in which a hind paw and contralateral fore paw are simultaneously in stance or swing phase. Trot.

Left/Right Coupling (hind, fore)=Left-right alternation rhythm. Ratio of time difference between consecutive left and right ground contacts to whole stride duration.

L/R Coupling Deviation (hind, fore)=Deviation of Left/Right Coupling between the strides.

Step Width (hind, fore)=The distance between left and right hind/fore paw during stance phase, perpendicular to midline.

Step Width Deviation (hind, fore)=The deviation of Step Width between the strides.

Double Support (hind, fore)=Percentage of stride time the both left and right (hind or fore) limbs simultaneously are in ground contact.

Single Support (hind, fore)=Percentage of stride time when one limb of the hind/fore limb pair is in ground contact and the other is not.

Support Zero=Percentage of stride time none of the four limbs are in ground contact (and all four limbs in mid air).

Support Single=Percentage of stride time one of the four limbs is in ground contact (three in mid air).

Support Diagonal/Girdle/Lateral=Percentage of stride time two of the four limbs are in ground contact, three modes: diagonal, girdle (galloping), lateral.

Support Three=Percentage of stride time three of the four limbs are in ground contact (one in mid air).

Support Four=Percentage of stride time all the four limbs are in ground contact.

Body Posture:

Toe Clearance (hind, fore)=Maximum clearance, i.e., distance from the ground, of a paw during swing phase.

Iliac Crest Height=Height of iliac crest during mid-stance.

Mean Hip Height=Average height of hip over a stride.

Hip Height Range=Range of hip height (vertical movement) during a stride.

Mean Hip Jerk=The average degree of non-smoothness, i.e., rate of acceleration change, of hip during stride.

Tail Base Height (min, mean, max)=Minimum, average, and maximum height of tail tip from the ground.

Tail Base Height Range=Range of vertical tail base movement during a stride.

Protraction (hind)=Maximum protraction of hind paw with respect to iliac crest point (forward direction, occurs at initial contact).

Retraction (hind)=Maximum retraction of hind paw with respect to iliac crest point (backward direction, occurs at initial swing).

Nose Height=Average height of nose.

Nose Height Range=Range of nose height during a stride.

Lateral Head Rotation=Average absolute value of lateral head rotation angle, based on head direction with respect to central line in horizontal plane.

Head Rotation Deviation=Deviation of Lateral Head Rotation between different strides.

Head Rotation Range=Range of Lateral Head Rotation angle in horizontal plane during a stride.

Tail Tip:

Tail Tip Height (min, mean, max)=Minimum, average, and maximum height of tail tip from the ground.

Tail Tip Height Range=Range of vertical tail tip movement during a stride.

Tail Tip Over Hip=Percentage of stride duration the tail tip is higher than hip level.

Tail Tip Ground Contact=Percentage of stride duration the tail tip touches ground.

Tail Tip Distance 2D=Ratio of two-dimensional tail tip trajectory length to stride length, determined from the side view.

Tail Tip Distance 3D=Ratio of three-dimensional tail tip trajectory length to stride length.

Joint Angles:

Hip Angle (min, mean, max)=Hip joint angle, minimum, mean, and maximum values.

Knee Angle (min, mean, max)=Knee joint angle, minimum, mean, and maximum values.

Ankle Angle (min, mean, max)=Ankle joint angle, minimum, mean, and maximum values.

Hip ROM=Hip joint range of motion (ROM) during a stride, difference between max and min Hip Angles.

Knee ROM=Knee joint range of motion during a stride.

Ankle ROM=Ankle joint range of motion during a stride.

Hip ROM Deviation=Deviation of hip ROM between different strides.

Knee ROM Deviation=Deviation of knee ROM between different strides.

Ankle ROM Deviation=Deviation of ankle ROM between different strides.

Paw Trajectory:

Paw Trajectory Shape 25% (hind, fore)=Percentage of swing phase duration the paw is above 25% of Toe Clearance.

Paw Trajectory Shape 50% (hind, fore)=Percentage of swing phase duration the paw is above 50% of Toe Clearance.

Paw Trajectory Shape 75% (hind, fore)=Percentage of swing phase duration the paw is above 75% of Toe Clearance.

Toe Lift-Off Angle (fore, hind)=Angle of paw trajectory ascent at the early swing phase.

Relative Trajectory Length=Ratio of fore paw 2D trajectory path length to stride length, subtracted by one.

Excess Vertical Movement=Ratio of vertical fore paw trajectory distance to double of Toe Clearance, subtracted by one.

Backward Paw Distance=Sum of excess backward movement of forepaw during a stride.

Example 4

Data Mining Based on Kinematic Gait Data

Data mining was successfully performed to extend the multivariate kinematic data analysis and capture the analgesic effect of cannabichromene (CBC) on quantitative measurement of parameters attributed to the temporal aspects of motion to evaluate temporal aspects of motion, such as positions, angles, velocities, and accelerations of body segments and joints during motion.

Overall, 97 gait parameters were analyzed, and each parameter was averaged within each treatment group. A statistical method using Contrastive Principal Component Analysis (cPCA) was employed (Abid et al., 2018). The method of cPCA was designed to identify different combinations of original variables linked to the Spinal Nerve Ligation (SNL) model effect (pain) and learning effect. An orthogonalization procedure was then performed to create the obtained effects independent of learning and possible sedation. After the contrastive principal components (cPCs) (Model, Sedative) were established, the corresponding cPC scores were computed for each observation. The obtained cPC scores were further analyzed by using mixed two-way ANOVA followed by Dunnett's test of the estimated marginal means. The cPCA based analysis framework was implemented using R environment (R version 3.6.3). Statistical analysis was performed using lme4 (Bates et al., 2015) and emmeans (R package version 1.4.5.) packages. The results of these comparisons were obtained by using all the previously identified components: model effect, learning effect and model orthogonal to learning.

FIG. 16 models the neuropathic pain effects versus sedative effects on different axes. Cannabinoid groups may demonstrate treatment effects in the pain axis (Y-axis), while simultaneously, there might be a change in sedative effects (X-axis). The groups shown are: SNL+Vehicle (as a control for SNL—induced pain score); SNL+Cannabinoids versus Baseline (BL—healthy control).

FIG. 17 shows the orthogonalization process of two components: SNL model effect and learning effect. The SNL Model effect and Learning effect share some common features (Left) and following the orthogonalization (Right), the learning effect (D7-D9) is "cleaned" from the SNL model effect (D7-BL), illustrating the shared features of SNL Model effect and Learning effect. The SNL Model orthogonal to the Learning effect is shown with the upper dashed arrow.

Results

The data mining conducted with this analysis reveals the impact on kinematic gait attributable to the cannabinoid analgesic effect.

FIG. 18 shows the final analgesic effect of CBC from 0 to 24 hours after a single-dose treatment with 10 mg/kg of CBC (p.o). Data is analyzed based on SNL model effects orthogonalized against the learning effect. Data are presented as mean±SEM. Statistical significances: * $p<0.05$ (two-way mixed ANOVA followed by Dunnett's test). BL: Baseline; D8 5 h: Day 8 post-surgery at 5 hours post-treatment; D8 9 h: Day 8 post-surgery at 9 hours post-treatment; D9: Day 9 (24 hours post-dosing).

The SNL model score indicates a significant analgesic effect of CBC at 10 mg/kg, and show reversal of SNL-induced pain at Day 8 up to 5 hours (D8 5 h) post-dosing as compared to vehicle group ($p<0.05$). This analgesic effect was not extended past 5 hours post-treatment which could be due to short half-life of CBC (data not shown).

FIG. 19 shows the sedation effect orthogonal to the SNL model effect. Data are presented as Mean±SEM. Statistical significances: * $p<0.05$ (two-way mixed ANOVA followed by Dunnett's test). BL: Baseline; D8 5 h: Day 8, 5 hours post-treatment; D8 9 h: Day 8, 9 hours post-treatment; D9: Day 9; PD: Post-dosing.

The independent sedation effect scores (orthogonal to both SNL model and learning effects) established a significant sedative effect for CBD:THC 10:10 mg/kg treatment group at D8, 5 h and D8, 9 h post-dosing, while CBC did not exert any sedative effect in animals (FIG. 19). This finding was consistent with the evF assay outcomes.

FIG. 20 depicts analgesic vs. sedative effect scores presented as XY-plot. The overall analgesic vs. sedative effect of each treatment 5-24 hours post-dosing (gait cycles averaged) is shown. The final independent sedation score is presented on X-axis and final analgesic score (inverted final SNL model score) on Y-axis. Each small dot represents one animal (average of analyzed gait cycles). Large dots illustrate the group means for Vehicle group, Pregabalin treatment (50 mg/kg), and CBC (10 mg/kg) from left to right: D8 5 h (8.5) post-dosing, D8 9 h (8.9) post-dosing; Day 9 post-dosing, respectively.

FIG. 21 depicts analgesic vs. sedative effect scores presented as XY-plot. The overall analgesic vs. sedative effect of each treatment 5-24 hours post-dosing showing the animals' individual steps. The final independent sedation score is presented on X-axis and final analgesic score (inverted final SNL model score) on Y-axis. Each small dot represents one animal (individual analyzed gait cycles). Large dots illustrate the group means (individual steps recorded) for Vehicle group, Pregabalin treatment (50 mg/kg), and CBC (10 mg/kg) from left to right: D8 5 h (8.5) post-dosing, D8 9 h (8.9) post-dosing; Day 9 post-dosing, respectively.

FIG. 20 and FIG. 21 exhibit XY-plots of the overall analgesic vs. sedative effect of each treatment 5-24 hours post-dosing considering gait cycles averaged or individual steps, respectively.

Conclusion

Data mining successfully determined the analgesic effect and sedative effect of multiple treatments by comparing 97 different gait parameters in each animal.

The final SNL model effect (or SNL-induced neuropathic pain) was most distinctively associated with the following parameters: increased vertical hip movement, gait asymmetries, and increased hind limb toe clearance.

CBC demonstrated a significant recovery in SNL model effect score (analgesic effect) 5 hours after a single-dose treatment with cannabichromene. No significant analgesic effect was indicated at 9 hours post-dosing, which may be due to short half-life of CBC (FIG. 18). This finding supports the notion that recovery in the SNL model score is associated with the analgesic treatment effect and supports SNL model stability.

The data analysis identified the fine motor kinematic parameters associated with sedation, such as increased stance and swing times, increased double support and decreased swing speeds or decreased tail base height. These results verified that CBC does not cause sedation (FIG. 19).

CBC demonstrated a significant analgesic effect at Day 8 5 h post-dosing with a single dose treatment of 10 mg/kg CBC (p.o.). This analgesic effect was qualitatively superior to the analgesic effect of pregabalin.

The data mining indicated that pregabalin treatment at 50 mg/kg exhibited no analgesic or sedative effect in fine motor kinematic performance of animals. This lack of efficacy of pregabalin in pain management was consistent with the results of the evF test when the time points were analyzed separately. The only significant effect of pregabalin was found in the area under curve (AUC) analysis of evF.

CBC demonstrated a marked reversal of SNL-induced pain as indicated by parameters associated with improvement in interlimb coordination, enhanced body posture, and rectified knee and ankle angles.

These results demonstrate that the use of a formulation for pain management with cannabichromene (CBC) as the primary cannabinoid, that is essentially free of Δ9-tetrahydrocannabinol (THC) can achieve an analgesic effect without any sedative effect. This can be particularly important to contribute to the total sedative load score of the medications prescribed.

CBC exhibited a marked reversal of motor impairments indicated by changes in motor skill parameters associated with improvement in interlimb coordination, enhanced body posture, and rectified knee and ankle angles. This finding may offer a practical guide to study motors skill changes in clinical setting in patients with chronic pain.

Example 5

The Effects of Single- and Repeated-Dose Treatment with Cannabichromene on Chemotherapy-Induced Pain Management In this Example, the effects of single-dose and repeated-dose treatment with cannabichromene (CBC) are assessed on chemotherapy-induced pain management a pain model involving Oxaliplatin (OXP). The CBC formulation described herein was compared with a known pain relieving medication, Duloxetine. Duloxetine is medicine within a class of drugs referred to as serotonin-norepinephrine reuptake inhibitors (SNRIs).

Methods

Model Induction—Mouse Oxaliplatin-induced polyneuropathy (OIPN) model was induced over a three-week period. The day of first Oxaliplatin (OXP) injection is referred to as day 0 (DO). OXP was administered as six separate intraperitoneal injections at 4.5-mg/kg (10 ml/kg, i.p.) to Groups 2, 3, and 4 on DO, D4, D8, D12, D16, and D20. The cumulative OXP dose was thus 27 mg/kg. The in-life procedures, such as observations, tests, and/or measurements were performed by Charles River Discovery Services with blinded methods. The mice were distributed into 4 groups (n=8 for Vehicle Control; n=10 OXP Control; n=20 CBC; n=15 Duloxetine).

Table 9 shows the planned and accomplished group sizes for this example.

TABLE 9

| Planned and Accomplished Group Sizes (N) | | | |
| --- | --- | --- | --- |
| Group # | Group | Planned N | Actual N |
| 1 | Veh.-Veh | 8 | 8 |
| 2 | OXP-Veh. | 10 | 10 |
| 3 | OXP-CBC | 20 | 18 |
| 4 | OXP-Dulx. | 15 | 13 |

Measurement of Plasma Bile Acid Concentration—A significant percentage of C57BL/6J mice have a portosystemic liver shunt, which results in major alteration of brain morphometry, brain metabolites, physiological readouts (such as body weight and liver enzymes), and cognitive deficits. Prior to study initiation, plasma bile acid measurement was performed to exclude animals with abnormally high bile acid concentration (>15 μmol/L), which is a surrogate marker of the portosystemic liver shunt (Cudalbu et al. 2013). The bile acid concentrations were analyzed by an outsourced third-party, using Thermofisher Konelab Xti 20™ according to manufacturer's instructions.

Body Weight—Animal body weights were measured before assigning the treatment groups and then on each day of the study. The last body weight measurement was performed upon endpoint sampling. Terminal body weights were not collected from animals found dead or euthanized moribund.

Treatments—Following exposure to OXP for 20 days, Groups 3 and 4 were treated with CBC (20 mg/kg, p.o.) and Duloxetine (25 mg/kg, i.p.), respectively, for 10 consecutive days. In a similar regimen Groups 1 and 2 (Vehicle Control and OXP-Vehicle Control, respectively) received a corresponding volume of 5% glucose solution at an administration volume of 10 mL/kg.

Acetone Cooling Test (ACT)—To produce a measurable cooling sensation, 10-15 μL of acetone was applied onto the medial area of the plantar hind paw with a 0.5 ml insulin syringe. Responses of a mouse to acetone were monitored for 20 s, and a score given based on a four-point scale (0-3 points), according to the response intensity, continuation, and briskness. The higher the score, the greater the cool allodynia sensed by the mouse.

Within one test timepoint, a total of 3 trials were performed per paw with a minimum gap of 5 min between testing. The three individual scores were added up to obtain a single score over a cumulative period of 60 s. Thus, for one test, the minimum score of one paw is 0 (no cool allodynia), while the maximum possible score is 9 (intensive cool allodynia). The total scores for the left and right paws were averaged to accomplish a single result value per mouse at each timepoint.

The Acetone Cooling Test was performed prior to OXP administration (Baseline), following the last OXP injection (D21), one day after the first CBC, Duloxetine, or Vehicle treatment (D22), and after a 10-day daily dosing of CBC, Duloxetine, or Vehicle treatment (D31). Taken together, the ACT was used to assess chemotherapy-induce cool allodynia as stated in the schedule:

Test days: Baseline, D21, D22, D31 (D0=day of first OXP injection).

Baseline: Measure cool allodynia as a baseline in healthy animals.

On D21: Test for accomplished cool allodynia level after OXP challenge.

On D22: At 60 min after the first Vehicle/CBC dose and 120 min after Dulx dose.

On D31: At 60 min after the last Vehicle/CBC and 120 min after Dulx dose.

Prior to the ACT, mice underwent 30-60 min habituation in the test room and approximately 30-60 min habituation in the test chambers. Before baseline ACT, mice were pre-handled for 2 min on two consecutive days in their main-tenance room for the purpose of decreasing false oversen-sitivity.

Results

Body weight and Welfare—Out of a total of 90 mice, 76 were accepted for the baseline tests as they displayed normal plasma bile acid contents—i.e. 24 mice were disqualified from the study due to very high BA concentration in plasma, indicating the portosystemic shunt. Seven mice were dis-qualified from further study due to showing too mild cool allodynia. Furthermore, the welfare observations made upon testing found that Duloxetine caused the most adverse effects, as 30% of the group displayed enlarged staring eyes and clearly decreased activity.

Oxaliplatin chemotherapy does not dramatically affect the body weight (BW) development. The raw BW values were normalized by the baseline weight, to obtain % BW Change from Baseline. The group means of this value are shown in FIG. 22.

FIG. 22 shows body weight development presented as Mean % BW Change from Baseline. Data are presented as mean±SEM. Two-way ANOVA, Sidak's multiple compari-sons test is used for comparisons to Vehicle-Vehicle vs. OXP-Vehicle *$p<0.001$; $p<0.01$; *$p<0.05$ Base=Baseline. The x-axis indicates the mean baseline BW. For simplicity, the vertical lines indicate the end of OXP exposure (D21) and the beginning of the Veh./CBC/Dulx dosing (D22).

During the OXP exposure period, a slight weight gain of a few percentages is seen (compared to approximately 10% on Veh.-Veh. group). From D22 onwards, all groups display a slight decrease in body weight that starts increasing—depending on the group. A slower increase in body weight observed in CBC and duloxetine—treated groups may be due to the loss of appetite that can potentially be due to the treatment.

Acetone Cooling Test—FIG. 23 shows timepoint-com-parison of ACT scores within each treatment group. Highly significant cool allodynia was induced by OXP in all treatment groups (FIG. 23; Baseline vs. D21). Upon the single dose treatment (D22) test timepoint, the CBC treatment group showed the most significant reversion of cool allo-dynia compared to D21 pre-treatment ($p<0.001$). Although Duloxetine induced a significant reversion of cool allodynia, it did not reach the same significance level as the CBC treatment group ($p<0.01$).

FIG. 23 provides a within treatment group comparison of mean ACT scores at indicated timepoints. Data are presented as mean+SEM. Two-way ANOVA, Dunnett's multiple com-parisons testis used for comparisons to D21 (pre-treatment). **$p<0.0001$; *$p<0.001$; **$p<0.01$; *$p<0.05$ Base=Baseline.

Moreover, 10-day repeated dosing with CBC showed significant reversion of cool allodynia (D31 vs. D21). Simi-larly, repeated dosing with Duloxetine showed a significant reduction of cool allodynia (D31 vs. D21) (FIG. 23).

FIG. 24 shows between treatment group comparison of mean ACT scores after an acute single dose (D22) or chronic repeated dosing (D31). Acute dosing with CBC or Duloxetine showed a statistically significant and comparable reduction in cool allodynia as compared with the OXP-Vehicle control. At the chronic dosing timepoint (D31), Duloxetine maintained a significant reduction in cool allo-dynia, whereas a qualitative but not statistically significant reduction was still observed for CBC treatment ($p=0.06$; FIG. 24).

FIG. 24 provides a between treatment group comparison of mean ACT scores at indicated timepoints. Data are presented as mean±SEM. ** $p<0.01$; * $p<0.05$, compared to the OXP-Veh. at the same timepoint (Mann-Whitney test); ###$p<0.001$; ##$p<0.01$, OXP-Veh. compared to Veh-Veh. at the same timepoint (Mann-Whitney test).

Conclusion

The formulation was shown to be as effective at managing pain, relative to a known pain relieving medication.

After the Oxaliplatin (OXP) exposure period, all OXP-treated groups displayed highly robust OIPN model induc-tion as confirmed by the acetone cooling test (ACT).

CBC (20 mg/kg) or Duloxetine (25 mg/kg) showed a comparable and significant reversion in chemotherapy-in-duced pain upon single-dose treatment as measured by the ACT.

Upon chronic multiple-dose treatment for 10 days, both CBC and Duloxetine caused a significant reduction in Oxa-liplatin-induced pain as measured in the ACT, as compared to the corresponding Vehicle control (Veh-OXP) group.

Of note, Duloxetine is the only recommended treatment for chemotherapy-induced peripheral neuropathy (CIPN) by the American Society of Clinical Oncology and the system-atic review of treatments for CIPN show evidence for a moderate benefit of duloxetine (Hou et al. 2018). However, Duloxetine therapy causes significant side-effects. In accor-dance, in this study pronounced adverse effects were observed in 30% of the Duloxetine group, which included enlarged staring eyes and obvious decreased overall activity. Significantly, CBC treatment caused no hyper-reactivity or psychoactive adverse effects.

These results affirm that a formulation comprising CBC can effectively achieve pain management for subjects expe-riencing neuropathic pain.

In the preceding description, for purposes of explanation, numerous details are set forth in order to provide a thorough understanding of the embodiments. However, it will be apparent to one skilled in the art that these specific details are not required. References cited herein are incorporated by reference.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

The following documents are herein incorporated by reference.

WO2016/044370 A1
WO2013/165251 A1
WO2012/144892 A1
WO2012/160358 A1
WO2007/083098 A1
US2016/0106705
US2016/0360721
US2018/0193304

Abid et al. "Exploring patterns enriched in a dataset with contrastive principal component analysis." *Nature Communications* 9.1 (2018): 1-7.

Bates, Douglas; Martin Maechler; Ben Bolker; Steve Walker (2015). Fitting Linear Mixed-Effects Models Using lme4. *Journal of Statistical Software,* 67(1), 1-48. doi:10.18637/jss.v067.i01.

Colloca L, et al., 2017. "Neuropathic Pain". *Nat Rev Dis Primers.* February 16; 3: 17002.

Crippa J A, Crippa A C, Hallak J E, Martin-Santos R, Zuardi A W. 2016. "Δ9-THC intoxication by cannabidiol-enriched cannabis extract in two children with refractory epilepsy: full remission after switching to purified cannabidiol." *Front. Pharmacol.* 7:35.

Crippa J A, Guimeraes F S, Campos A C, Zuardi A W. 2018. "Translational Investigation of the Therapeutic Potential of Cannabidiol (CBD): Toward a New Age." *Fron. Immunol.* September 21; 9: 02009.

Cudalbu C, McLin V A, Lei H, et al. "The C57BL/6J mouse exhibits sporadic congenital portosystemic shunts". *PLoS One.* 2013; 8(7): e69782. Published 2013 Jul. 23. doi: 10.1371/journal.pone.0069782.

De Petrocellis L, Ligresti A, Moriello A S, Allara M, Bisogno T, Petrosino S, Stott C G, Di Marzo V. 2011. "Effects of cannabinoids and cannabinoid-enriched Cannabis extracts on TRP channels and endocannabinoid metabolic enzymes." *Br J Pharmacol* 163: 1479.

Guimaraes F S, Chiaretti T M, Graeff F G, Zuardi A W. 1990. "Antianxiety effect of cannabidiol in the elevated plus-maze". *Psychopharmacology* (1990)100: 558-9.

Hou S, Huh B, Kim H K, Kim K H, Abdi S. "Treatment of Chemotherapy-Induced Peripheral Neuropathy: Systematic Review and Recommendations". *Pain Physician.* 2018; 21(6):571-592.

Izzo A A, Borrelli F, Capasso R, Di Marzo V, Mechoulam R. 2009. "Non-psychotropic plant cannabinoids: new therapeutic opportunities from an ancient herb." *Trends Pharmacol Sci* 30: 515.

Izzo, A A, and Aviello G, Borrelli F, Romano B, Piscitelli F, Gallo L, Capasso F, Orlando P, Di Marzo V Capasso R. 2012. "Inhibitory effect of cannabichromene, a major non-psychotropic cannabinoid extracted from *Cannabis sativa*, on inflammation-induced hypermotility in mice." *Br J Pharmacol* 166(4):1444-60.

Kim, S H, and Chung J M. 1992 "An experimental model for peripheral neuropathy produced by segmental spinal nerve ligation in the rat." *Pain.* September; 50(3):355-63.

Lewis M A, Russo E B, and Smith K M. 2017. "Pharmacological foundations of cannabis chemovars." *Planta Med.* 84: 225-233.

Maione S, Piscitelli F, Gatta L, D. Vita, L. De Petrocellis, E. Palazzo, V. de Novellis, V. Di Marzo. 2011. "Non-psychoactive cannabinoids modulate the descending pathway of antinociception in anaesthetized rats through several mechanisms of action." *Br. J. Pharmacol.* 162: 584-596.

Mandolini G M, Lazzaretti M, Pigoni A, Oldani L, et al. 2018. "Pharmacological properties of cannabidiol in the treatment of psychiatric disorders: a critical overview." *Epidemiol Psychiatr Sci.* 27(4):327-335.

Morales P, Hurst, D. P., and Reggio, P. H. 2017. "Molecular targets of the phytocannabinoids-a complex picture." *Prog. Chem. Org. Nat. Prod.* 103-131.

Musty, R. E. and Deyo, R. A. (2003) "Cannabichromene (CBC) extract alters Behavioral Despair on the Mouse Tail Suspension test of depression", *Proceedings* 2003 *Symposium on the Cannabinoids,* Burlington, VT International Cannabinoid Research Society, p. 146.

Patel, S., Hill, M. N., Cheer, J. F., Wotjak, C. T., and Holmes, A. 2017. "The endocannabinoid system as a target for novel anxiolytic drugs." *Neurosci. Biobehav. Rev.* 76: 56-66.

Russo, E B. 2011. "Taming THC: potential cannabis synergy and phytocannabinoid-terpenoid entourage effects." *Br J Pharmacol* 163:1344.

Shinjyo N, Di Marxo V. 2013. "The effect of cannabichromene on adult neural stem/progenitor cells." *Neurochemistry International* 63(5): 432-437.

Wolf S A, Bick-Sander A, Fabel K, Leal-Galicia P, Tauber S, Ramirez-Rodriguez G, et al. 2010. "Cannabinoid receptor CB1 mediates baseline and activity-induced survival of new neurons in adult hippocampal neurogenesis." *Cell Commun Signal.* 8:12.

What is claimed is:

1. A formulation for use in pain management by administration to a subject in need thereof, said formulation comprising a primary cannabinoid and an excipient, diluent or carrier;

wherein said primary cannabinoid consists of cannabichromene (CBC), wherein said formulation is essentially free of tetrahydrocannabinol (THC), and wherein the pain management comprises an analgesic effect without a sedative effect.

2. The formulation for use in pain management by administration to a subject in need thereof according to claim 1, wherein the pain management comprises treatment of pain due to neuropathic pain, cancer, chemotherapy, inflammation, diabetes, diabetic neuropathy, post-shingles neuralgia, peripheral neuropathy, multiple sclerosis, injury, accident, surgery, or tissue damage.

3. The formulation for use in pain management by administration to a subject in need thereof according to claim 1, additionally comprising one or more secondary cannabinoids present in an amount of up to 15% by weight of the primary cannabinoid, wherein the one or more secondary cannabinoids comprises cannabidiol (CBD).

4. The formulation for use in pain management by administration to a subject in need thereof according to claim 1, wherein the formulation is prepared in a dosage form of a pill, tablet, gel capsule, syrup, oil-based spray, or liquid oil form.

5. The formulation for use in pain management by administration to a subject in need thereof according to claim 1, wherein the formulation provides a total amount of from 1 mg to 25 mg of primary cannabinoid per dose.

6. A method for pain management in a subject in need thereof, comprising administering to said subject an effective amount of a formulation comprising a primary cannabinoid and an excipient, diluent, or carrier;

wherein said primary cannabinoid consists of cannabichromene (CBC), wherein said formulation is essentially free of tetrahydrocannabinol (THC); and wherein the pain management comprises an analgesic effect without a sedative effect.

7. The method according to claim 6, wherein the pain management comprises alleviating pain due to neuropathic pain, cancer, chemotherapy, inflammation, diabetes, diabetic neuropathy, post-shingles neuralgia, peripheral neuropathy, multiple sclerosis, injury, accident, surgery, or tissue damage.

8. The method according to claim 6, wherein the formulation additionally comprises one or more secondary cannabinoids present in the formulation in an amount of up to 15% by weight of the primary cannabinoid, and wherein the one or more secondary cannabinoids comprises cannabidiol (CBD).

9. The method according to claim 6, wherein the formulation is administered in a dosage form of a pill, tablet, gel capsule, syrup, oil-based spray, or liquid oil form.

10. The method according to claim 6, wherein the formulation provides to the subject a total amount of from 1 mg to 25 mg of primary cannabinoid per dose.

11. The method according to claim 10, wherein the formulation provides to the subject a total amount of from 5 mg to 20 mg of primary cannabinoid per dose.

12. The formulation for use in pain management by administration to a subject in need thereof according to claim 5, wherein the formulation provides a total amount of from 5 mg to 20 mg of primary cannabinoid per dose.

13. The formulation for use in pain management by administration to a subject in need thereof according to claim 1, wherein said formulation comprises cannabichromene (CBC) and an excipient, diluent or carrier;

wherein said formulation comprises 1% or less by weight of THC as compared to CBC.

14. The method for pain management according to claim 6, wherein said formulation comprises cannabichromene (CBC) and an excipient, diluent or carrier;

wherein said formulation comprises 1% or less by weight of THC as compared to CBC.

\*　\*　\*　\*　\*